(12) United States Patent
Nur et al.

(10) Patent No.: US 9,427,490 B2
(45) Date of Patent: Aug. 30, 2016

(54) GELATIN SPONGE COMPRISING AN ACTIVE INGREDIENT, ITS PREPARATION AND USE

(71) Applicant: Omrix Biopharmaceuticals Ltd., Rehovot (IL)

(72) Inventors: Israel Nur, Moshav Timmorim (IL); Liliana Bar, Rehovot (IL); Guy Tomer, Modiin (IL); Eyal Sheetrit, Shoham (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 0 days.

(21) Appl. No.: 14/869,311

(22) Filed: Sep. 29, 2015

(65) Prior Publication Data

US 2016/0136322 A1 May 19, 2016

Related U.S. Application Data

(62) Division of application No. 14/615,538, filed on Feb. 6, 2015, now abandoned, which is a division of application No. 13/847,898, filed on Mar. 20, 2013, now Pat. No. 8,981,058, which is a division of application No. 12/920,000, filed as application No. PCT/IL2009/000236 on Mar. 2, 2009, now Pat. No. 8,475,812.

(60) Provisional application No. 61/033,174, filed on Mar. 3, 2008.

(51) Int. Cl.
*A61L 15/42* (2006.01)
*A61K 9/70* (2006.01)
*A61K 38/48* (2006.01)

(52) U.S. Cl.
CPC .......... *A61L 15/425* (2013.01); *A61K 38/4833* (2013.01)

(58) Field of Classification Search
None
See application file for complete search history.

(56) References Cited

U.S. PATENT DOCUMENTS

| | | | |
|---|---|---|---|
| 2,558,395 A | 6/1951 | Studer | |
| 4,265,233 A | 5/1981 | Sugitachi et al. | |
| 4,292,972 A | 10/1981 | Pawelchak et al. | |
| 4,522,057 A | 6/1985 | Kerchiss | |
| 5,143,838 A | 9/1992 | Kraus et al. | |
| 5,643,596 A | 7/1997 | Pruss et al. | |
| 6,971,813 B2 | 12/2005 | Shekalim et al. | |
| 8,981,058 B2 | 3/2015 | Nur et al. | |
| 2004/0062592 A1 | 4/2004 | Shekalim et al. | |

FOREIGN PATENT DOCUMENTS

| | | |
|---|---|---|
| EP | 0378798 | 7/1990 |
| EP | 0277096 | 7/1992 |
| EP | 0 568 334 A1 * | 11/1993 |
| EP | 0596215 | 5/1994 |
| JP | 6-142177 | 5/1994 |
| JP | 7-500095 | 1/1995 |
| JP | 8-500334 | 1/1996 |
| JP | 9-504719 | 5/1997 |
| JP | 2008-505132 | 2/2008 |
| WO | 90/13320 | 11/1990 |
| WO | 93/06855 | 4/1993 |
| WO | 93/21908 | 11/1993 |
| WO | 95/12371 | 5/1995 |
| WO | 02/072128 | 9/2002 |
| WO | 2006/005340 | 1/2006 |
| WO | 2009/109194 | 9/2009 |

OTHER PUBLICATIONS

International Preliminary Report on Patentabilty re: PCT/IL2009/000236 dated Sep. 7, 2010.

International Search Report re: PCT/IL2009/000236 dated Jun. 26, 2009.

Streule, W. et al. 'Pipejet: A Simple Disposable Dispenser for the Nano- and Microliter Range' J. of Assoc. Lab Automation (2004) vol. 9 pp. 300-306.

* cited by examiner

*Primary Examiner* — Suzanne M Noakes

(74) *Attorney, Agent, or Firm* — David R. Crichton

(57) ABSTRACT

The present invention is directed to a method for manufacturing a cross-linked gelatin sponge having a surface by providing a cross-linked gelatin sponge, wetting the surface of the sponge by applying a sufficient amount of liquid comprising a protein or peptide active ingredient, wherein a sufficient amount of liquid is one that retains the flexibility of the sponge even after drying. The sponge is then dried the sponge to obtain a flexible, dry and ready to use cross linked gelatin sponge having a layer of protein or peptide active ingredient on the surface thereof.

4 Claims, 10 Drawing Sheets

GELATIN SPONGE COMPRISING AN ACTIVE INGREDIENT, ITS PREPARATION AND USE

FIELD OF THE INVENTION

The invention relates to an improved dry and flexible cross-linked gelatin sponge comprising a layer of active ingredient and uses thereof.

BACKGROUND OF THE INVENTION

Rapid blood loss from relatively large surfaces is particularly difficult to control since it cannot be controlled by sutures or other ligation means. Attempts have been made to develop a haemostatic sponge which provides a fast and effective composition for inducing rapid blood coagulation and haemostasis at a wound or bleeding site. One such haemostatic sponge composition is an absorbable gelatin sponge. The spongy physical properties of the gelatin sponge hasten clot formation and provide structural support for the forming clot.

Gelatin sponges are made by whipping a solution of gelatin and drying the foam, usually by lyophilization. Unlike collagen which is naturally insoluble in aqueous neutral solutions, gelatin is soluble at temperatures above 30° C., especially at 37° C., the physiological temperature. This characteristic renders the sponge unsuitable for in vivo use as the sponge would dissolve quickly and loss its structural integrity and porous structure. The gelatin must therefore be cross-linked in order to prevent its rapid dissolution in the blood. Methods of cross linking include treatment of the sponge with a chemical cross-linking agent such as formaldehyde, glutaraldehyde, and carbadiimides (e.g. EDC) or via treatment of the dry sponge with dry heat (100-160° C. for several hours).

While its mode of action is not fully understood, it is currently believed that its effect appears to be linked to the ability of the gelatin sponge to absorb and hold within its interstices, many times its weight of blood and other fluids. Caught blood platelets interact with the sponge and get activated leading to the formation of a haemostatic plug and cessation of bleeding. This haemostatic plug resembles the natural plug that usually forms in the body after injury. The activated platelets also initiate the coagulation cascade that ends with conversion of soluble fibrinogen into a net of insoluble fibrin by the action of thrombin. Factor XIII which is activated by thrombin in the presence of $Ca^{2+}$ cross-links and stabilizes the clot's fibrin monomers.

GELFOAM® and SURGIFOAM® are an example of haemostatic devices which can be applied dry or moistened with sterile saline or thrombin directly to the wounded site to obtain control of the bleeding. In order to enhance the natural haemostatic property of gelatin, products or kits that combine the haemostatic features of gelatin sponge, thrombin and $Ca^{2+}$ have been developed and manufactured. For example, it is customary that in surgery the gelatin sponge is removed from its package, dipped into diluted thrombin solution and kneaded vigorously until all air is expelled. This step is followed by a second immersion in thrombin solution and application of the wet sponge to the bleeding organ with light pressure. However, the soaking of the sponge requires time-consuming and cumbersome procedures, including thawing and predilution of the concentrated thrombin solution. Each of the preparation steps introduces potential errors which might compromise the sterile preparation and vary the efficacy of the sponge. Moreover, the complicated procedure requires administration of the sponge by trained emergency personnel. Another major drawback in that technique is that a large volume of liquid is required to fill the sponge voids consequently resulting in a low concentration of thrombin and $Ca^{2+}$ at the interface between the sponge and the injured site. As a result, the sponges are ineffective in providing and maintaining haemostasis. To overcome this problem, surgeons often resort to the use of high concentrations of thrombin, which may lead to local thrombotic events.

The following publications disclose coating of a cross-linked gelatin sponge with a solution of an active ingredient and drying the sponge.

U.S. Pat. No. 5,643,596 and WO9512371 disclose a haemostatic patch comprising a matrix such as absorbable gelatin sponge and an effective amount of epsilon aminocaproic acid (EACA) on only one side of the matrix. According to the description the matrix can be coated before and after addition of EACA with thrombin solution. The EACA can be applied by spraying powder, by coating a solution onto the matrix, or by complete or partial dipping. Drying of the wetted sponge is accomplished preferably by lyophilization. The patent application emphasizes the importance of EACA in the patch and is silent on a biodegradable matrix without EACA.

WO9013320 relates to a haemostatic sponge comprising a porous structure of biologically absorbable solid material such as denatured gelatin sponge, thrombin, and one or more thrombin-stabilizing agents. The hemostatic sponge is prepared by introducing into the sponge by injection at a multiplicity of sites an aqueous solution of thrombin. The injection is carried out without resulting in leakage of the injected liquid to the surfaces of the sponge material. The sponge is then air-dried at a temperature of 30-100° C. for a time a period sufficient to reduce the water content to below 50%. According to the description, the injection of the thrombin solution may result in structural deformation of the sponge.

U.S. Pat. No. 2,558,395 discloses a ready-to-use gelatin sponge containing thrombin. According to the patent, thrombin is added to an aqueous gelatin solution, transformed into foam and dried in vacuum at low temperature. The gelatin in this patent was not cross-linked at any stage during the preparation. Thus, upon contact with blood, the gelatin component is dissolved, the thrombin is released immediately and causes the transformation of fibrinogen to fibrin and a fibrin film is formed over the wound.

U.S. Pat. No. 4,292,972 relates to a lyophilized foam sponge product which has a hydrocolloid composition. According to the description the solubility and absorbability of the lyophilized foam product can be reduced by cross-linking either before or after the lyophilization procedure. The lyophilized foam product is formed from a mixture of gelatin, pectin and sodium carboxymethylcellulose.

U.S. Pat. No. 4,265,233 discloses a wound healing material to which factor XIII with or without thrombin have been fixed by covalent bonding, ionic bonding adsorption or entrapping. According to the description the wound healing material may be synthetic or natural polymers. The patent discloses several natural occurring proteins, including cellulose, viscose rayon, cupraammonium rayon, cellulose acetate, carboxymethyl cellulose, methyl cellulose, agarose, dextran, pullulan, pectin, alginic acid, chitin, polysaccharides such as mucopolysaccharides, and proteins such as wool, silk, collagen, gelatin and casein. The examples disclose dipping of a gelatin sponge in the size of 5×2.5×0.5 cm in 10 ml of an aqueous solution of factor XIII with or without thrombin and subsequent freeze-drying for 20 hours.

EP0277096 discloses hemostatic materials, such as GELFOAM®, SURGICEL®, and AVICEL®, and collagen which can be effectively used in combination with a stabilized thrombin formulation. According to the patent, the preparation must contain polyols and at least one buffer such as acetate or phosphate buffer. According to the description the stabilized solution is preferably absorbed onto the hemostatic agent and the pad is freeze-dried and packaged in a sterile manner.

WO02072128 discloses a cross-linked gelatin composition which has a wetting agent incorporated therein. According to the description the wetting agents can be coated over the surface of the gelatin sponge. The examples show that addition of the wetting agent onto the surface of the sponge is carried out by placing the sponge into a vial containing a solution of a wetting agent and a solvent. The vial is then inverted to allow the solution to soak into the sponge. The coated composition is then removed, drained of excess liquid and air dried overnight. According to the description the gelatin composition may also include a medicament such as thrombin, fibrinogen, factor XIII and other coagulation factors.

EP0568334 relates to a collagen-containing sponge comprising an absorbable gelatin sponge, collagen, and an active ingredient. The absorbable gelatin sponge can be combined with the collagen and the active ingredient by transferring a predetermined amount of a collagen solution on top of the gelatin sponge. The example discloses a preparation of a collagen sponge by pipetting 0.24 or 0.4 ml of collagen solution containing platelet-derived growth factor (PDGF) on top of a 1 mm gelatin sheet. Following soaking, the sponge is dried, preferably, at room temperature for a period of about an hour to about five days. It is indicated in the patent that in order to improve flexibility of the sponge a suitable plasticizer can be used.

WO9306855 relates to a haemostatic composition comprising a hemostatically effective amount of factor VIIa together with a biologically compatible carrier such as a biodegradable sponge material. The carrier does not contain thrombin or any other blood clotting factor. The description discloses several materials for the preparation of the hemostatic sponges such as collagen, gelatin such as denatured gelatin, chitin, cellulose, polyglycolic acid and polyacetic acid. The sponge may be prepared by saturating a preformed dried sponge with a solution of FVIIa followed by freeze-drying. The examples disclose soaking of 5 mm cores of gelatin sponge in 2 ml of sterile water which contained factor VIIa. The wet sponge was applied to the bleeding site without drying.

SUMMARY OF THE INVENTION

Absorbable gelatin sponges are used in various surgical procedures to assist cessation of bleeding. It is currently believed that the haemostatic effect of the sponge is linked to the sponge porosity and to its ability to absorb blood. Moreover, due to the porosity of the sponge, blood platelets are caught and the coagulation cascade is activated transforming soluble fibrinogen into a net of insoluble fibrin which stops the bleeding. Thus, the sponge structure is believed to be essential for the mode of action of the sponge. In use, the gelatin sponge is dipped into a thrombin solution before application into the wounded tissue to enhance its haemostatic performance. This step is time-consuming, complicated, and results in a relatively low concentration of thrombin at the wound contacting surface.

To facilitate ease of use, a gelatin sponge which comprises thrombin can be supplied in a dry form. However, it was found according to the present invention that drying a wetted sponge results in collapse of the sponge and/or in modification of the original shape or the structural integrity of the sponge material. Also, it was found according to the invention that this structural modification reduces the ability of the sponge material to absorb blood and/or the ability of the sponge to easily conform to the shape of the body surface.

The present invention solves these problems since the liquid comprising the active ingredient is absorbed into the sponge at a small volume so that only a small portion of the sponge is wetted while the bulk of the sponge remains dry; consequently the original structural characteristics (e.g., thickness, texture and appearance) and the flexibility of the sponge are substantially retained subsequent to the drying procedure.

Furthermore, in the case of complete soaking the thrombin is dispersed within the interstitial voids of the sponge generating a low concentration of thrombin at the surface of the sponge which is in contact with the wound. As a result, the sponge is ineffective in aiding hemostasis. Advantageously, the present invention provides a sponge which contains a highly concentrated and thin layer of thrombin at the surface of the sponge.

The disclosed art do not relate to any problem of loosing flexibility or thickness of the sponge after wetting and drying; and neither suggests nor discloses the optimal limit liquid volume to be applied to the sponge during application of the active ingredient.

An object of the present invention is to provide a method for manufacturing an improved cross-linked gelatin sponge comprising a protein or peptide active ingredient comprising the steps of:
  a) providing a cross-linked gelatin sponge having at least one surface;
  b) homogenously applying a liquid comprising a protein or peptide active ingredient to said at least one surface of said sponge, wherein the volume of the liquid applied is equal to or less than 5% of the volume of the sponge in a); and
  c) drying the sponge,
  thereby obtaining a flexible, dry cross linked gelatin sponge comprising a stable layer of protein or peptide active ingredient on at least one surface of the sponge.

In one embodiment of the present invention, said liquid applying step is carried out in a single stage.

In another embodiment of the present invention, epsilon aminocaproic acid is absent from said liquid.

In another further embodiment of the present invention, said liquid applying step is carried out by using a roller.

Yet in another embodiment of the invention, said liquid applying step comprises the steps of:
  a) providing a rotating roller having an external surface, wherein at least a portion of said external surface is in contact with a reservoir comprising said liquid;
  b) rotating the roller to cover said external surface with said liquid;
  c) contacting said external surface of the roller with said at least one surface of said sponge; and
  d) moving said external surface of the roller and said at least one surface of said sponge relative with one another;
  thereby depositing said liquid onto said at least one surface of said sponge.

Yet in another further embodiment of the invention, said external surface includes a plurality of hollowed spaces capable of holding said liquid.

In one embodiment of the invention, said liquid applying step is carried out by using a liquid dispenser.

In another embodiment of the invention, said liquid applying step is carried out by using the PipeJet™-technology.

In another further embodiment of the invention, the thickness and the flexibility of the dried sponge are substantially similar to those found in the original gelatin sponge.

In another embodiment of the invention, at least 75% of the thickness of the original gelatin sponge is retained.

In another embodiment of the invention, the thickness of said layer is equal to or less than 24% of the overall thickness of the sponge following the drying step.

Yet in another embodiment of the invention, said drying step is carried out by a process selected from the group consisting of: vacuum oven, freeze-drying, and air drying.

Still in another embodiment of the invention, said drying step is carried out by vacuum oven.

In one embodiment of the invention, said active ingredient comprises thrombin. In another embodiment of the invention, the thrombin activity in said liquid is in the range of from about 2 to about 15,000 IU/ml, in the range of from about 2 to about 4,000 IU/ml, or in the range of from about 4,000 to about 10,000 IU/ml.

In another aspect, the invention relates to an improved dry cross-linked gelatin sponge comprising a layer of a protein or peptide active ingredient on at least one surface of the sponge, the layer having an average thickness of not more than about 24% of the overall thickness of the sponge, wherein said layer is stable and is substantially homogenously distributed throughout said surface; and the thickness and the flexibility of the sponge are substantially similar to that found in the original counterpart non-layered gelatin sponge.

In one embodiment of the invention, wetting agents are absent from said layer.

In another embodiment of the invention, the active ingredient comprises thrombin. The thrombin activity can be in the range of from about 1 to about 300 $IU/cm^2$, in the range of from about 10 to about 40 $IU/cm^2$, or in the range of from about 20 to about 40 $IU/cm^2$.

The sponge according to the invention can be used in surgery. In another embodiment of the invention, the sponge according to the invention can be used for promoting blood coagulation.

Another object of the invention is to provide a package containing a sterile cross-linked gelatin sponge according to the invention.

Still another aspect of the invention is to provide a method for promoting blood coagulation, comprising administering to a wound or a bleeding site a cross-linked gelatin sponge or using a package according to the invention.

The cross-linked gelatin sponge according to the invention can be used for promoting blood coagulation.

BRIEF DESCRIPTION OF THE DRAWINGS

The features, aspects, and advantages of the present invention will become better understood with regard to the following description, examples, claims, and the following figures.

DESCRIPTION OF EMBODIMENTS OF THE INVENTION

Figure 1A:
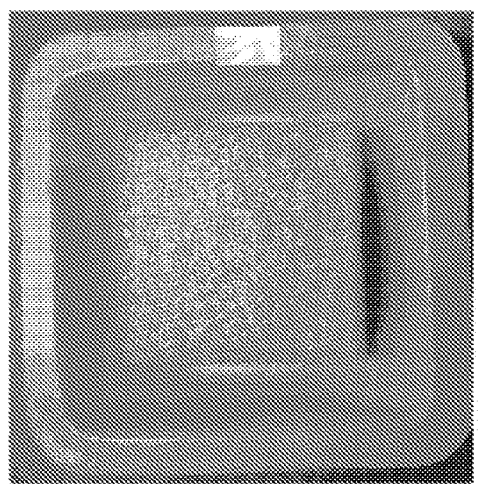
FIGS. 1A-D: show a top view of a gelatin sponge partially soaked in 500 μl saline (A; sponge No. 1) as compared to a sponge partially soaked in 500 μl distilled water+0.1% NP40 (B; sponge No. 2) following the drying procedure. A sided view of the sponges is shown in C and D (sponge No. 1 and 2, respectively).

In one aspect, the invention provides a method for manufacturing an improved dry and ready to use cross-linked gelatin sponge comprising a stable layer of protein or peptide active ingredient on at least one surface of the sponge.

Results obtained according to the invention show the advantages of a gelatin sponge comprising a layer of protein or peptide active ingredient on at least one surface of the sponge obtained by a method comprising the steps of: a) providing a cross-linked gelatin sponge, b) homogenously applying liquid comprising a protein or peptide active ingredient to at least one surface of the sponge. The volume of the liquid applied is equal or less than 5% of the initial volume of the sponge; and c) drying the sponge.

The term "improved gelatin sponge comprising a protein or peptide active ingredient" relates to a gelatin sponge which comprises a stable layer of a protein/peptide active ingredient on at least one surface, the layer is homogenously distributed throughout the surface of the sponge, and the sponge has a thickness and a flexibility which are substantially similar to those found in the original counterpart gelatin sponge.

The term "improved gelatin sponge comprising thrombin" relates to a gelatin sponge which comprises a stable layer of thrombin on at least one surface, the layer is homogenously distributed throughout the surface of the sponge, and the sponge has a thickness and a flexibility which are substantially similar to those found in the original counterpart gelatin sponge.

Throughout the description the term "thickness" is interchangeable with the term "height".

The acceptable volume of liquid to be applied to the sponge according to the invention is calculated as follows: for example, when using a sponge in the size of 2.5×2.5×1 cm (6.25 cm$^3$) which corresponds to a volume of 6250 µl, the liquid intake into the sponge should be equal or less than 312 µl. When applying liquid to more than one surface of the sponge, the volume should be equal or less than 5% of the volume of the sponge in each and every surface separately.

The term "initial volume of the sponge" relates to the volume of the sponge prior to the liquid applying step.

It was found according to the invention that drying a wetted sponge results in collapse of the sponge and that increasing the liquid uptake into the sponge significantly affected the overall thickness of the sponge after lyophilization or vacuum drying procedures. In fact, the liquid uptake volume during the wetting step was shown to be inversely proportional to the sponge thickness following a drying procedure. For example, increasing the amount of liquid uptake into the sponge e.g. by using surfactants, lead to a decrease in the overall thickness of the dried sponge.

The term "surfactant" refers to an agent which facilitates the wetting of the sponge or reduces the hydration time of the sponge. Examples of suitable surfactants include, but are not limited to, 0.01 and 0.1% NP40, 20% ethanol, and 0.02% Tween 20. The term "surfactant" is interchangeable with the term "wetting agent".

This decrease in thickness of the sponge results in structural modification of the sponge such as deformation, damaged integrity/porosity of the sponge and/or in modification of the mechanical characteristics of the sponge, such as flexibility. It was also found that this structural modification affected the ability of the sponge to absorb water, i.e., thin sponges, obtained by drying sponges which absorbed high levels of liquid during the wetting step, absorbed less water than thick sponges, prepared by drying sponges which absorbed low levels of water during the wetting step.

Of note, applying liquid to the sponge at a volume of equal or less than 5% of the initial volume of the sponge results in a liquid uptake/absorption of equal or less than 5% of the initial volume of the sponge.

The method allows preparation of a sponge according to the invention having a substantially unaltered absorption capability as compared to that found in the original counterpart non-layered gelatin sponge. Of note, the US Pharmacopeia indicates that, absorbable gelatin sponges should absorb not less than 35 times their weight of water. It was found according to the invention that in order to meet the pharmacopeia demand, a gelatin sponge such as SPONGOSTAN® having an initial thickness of 10 mm may retain a thickness of equal or more than 7.44 mm, after wetting and drying in order to absorb not less than 35 times its weight of water i.e. loss of thickness after wetting and drying the gelatin sponge should be not more than 26% from the initial height.

For example, when the initial thickness of the gelatin sponge is 10 mm, the overall thickness of the dry ready to use sponge according to the invention can be in the range of about 7 to about 9.8 mm, such as about 7.2, 7.3, 7.44, 7.5, 8, 8.2, 8.5, 9, and 9.5 mm, i.e. the sponge can retain from about 70 to about 98%, such as 73, 74, 75, 80, 82, 85, 90 and 95% from the initial height of the original gelatin sponge following the wetting and drying step.

Moreover, it was found according to the invention that in order to retain at least about 74% of the initial thickness, the volume of the liquid applied to SPONGOSTAN® sponges should be to an extent of equal or less than 5% of the volume of the sponge prior to the liquid applying step as defined above such as 4.5, 4, 3.5, 3, 2.5, 2%. For example, it was found that a pre-made gelatin dry sponge prepared with a 2.5×2.5×1 cm sponge that absorbed a small volume of liquid like up to about 220 µl when coated with the active ingredient, i.e. a calculated liquid uptake of less than 3.5% of the volume of the sponge, substantially unchanged its mechanical properties (e.g. flexibility) and structural characteristics (e.g. thickness) when compared to the original gelatin sponge. This sponge contained a highly concentrated and thin dry layer of active ingredient on its wound facing side which can be easily distinguished from the non-biology side of the sponge since it is less porous in appearance than the other non-treated faces of the sponge. The layer comprising the active ingredient is stable upon storage, and when wetted the active ingredient dissolves and diffuses out. The term "stable" refers to a layer which does not undergo flaking, for example, a layer which does not break and/or a layer which does not crumble into individual pieces.

In one embodiment of the invention, the stability of the layer can be assessed as follows: a specific size of the dry and ready to use sponge is cut and its weight is determined. The sample is then placed within a borosilicate glass scintillation vial while the layered surface is facing up and the vial is cupped. A support stand having an extension clamp, capable of holding a plastic tube, is then placed on a hard level surface. The plastic tube is inserted vertically into the clamps, the clamps are tightened and a solid silicone stopper is placed in the bottom of the plastic tube. A plastic block is placed underneath the stopper to prevent the stopper from being expelled during the measurement. Afterwards, the vial containing the sample is dropped 4 times from the top of the plastic tube with the cap side up and the sample is weighed. The dropping point was the same in all tests in order to exclude variability and ensure standardization. The powder loss is calculated by subtracting the post-drop weight of the sample from the pre-drop weight of the sample and the percentage of weight reduction of the sample is calculated by dividing the powder loss to the pre-drop weight and multiplying the result by 100. For example, when the size of the sample is about 1.7 cm² and the above stability test is carried out a desirable weight reduction of the sample is less than 5%.

It was also found according to the present invention that drying by lyophilization or vacuum drying procedures, both being methods which are currently used and are appropriate for use with protein/peptide ingredients, can affect the thickness of the layer on the surface of the sponge. The results show that 5% liquid uptake during the wetting step resulted in a dried top layer (or layer of the applied active ingredients) of 5.8-8.3% and 12.5-24% of the overall thickness of the sponge in the vacuum dried and lyophilized dried sponges, respectively. The results obtained indicate that for obtaining a sponge with a thinner layer of active ingredient and/or having the ability to slow-release active materials the vacuum drying procedure can be used. For obtaining a sponge with thicker layer of active ingredient the method of drying by lyophilization can be used.

The drying step can be carried out by any procedure known in the art which does not degrade or denature the active ingredients which are sensitive to thermal procedures including, but not limited to, vacuum drying, freeze drying and air drying such as room temperature drying.

Generally, using a vacuum drying procedure may offer several advantages over air drying and freeze drying. Drying at room temperature achieves a gradual decrease in the water content. Freeze drying substantially preserves the original structure of the sponge, however it is a complicated and an expensive form of drying. Vacuum drying is a cheap and fast procedure which substantially preserves the original porous structure of the sponge.

The findings according to the invention also show that when using thrombin as the active ingredient, the thrombin is released faster in the sponge prepared by complete soaking followed by lyophilization than in a sponge prepared by partial soaking and dried in a vacuum oven in which the thrombin was gradually released. At the end of the testing, both sponges had similar recovered activity indicating that the partial soaked sponge dried in a vacuum oven preserves the thrombin activity. An important advantage of the method according to the invention is that the activity of the active ingredient in the ready to use sponge is substantially preserved.

The term "partial soaking", as used herein, relates to applying liquid to at least one surface of the sponge wherein the volume of the liquid applied to the sponge is equal to or less than 5% of the initial volume of the sponge. The term "complete soaking" refers to applying liquid to the sponge wherein the volume of the liquid applied to the sponge is more than 5% of the initial volume of the sponge.

Another advantage of the sponge according to the invention is its flexibility. The flexibility enables the sponge to easily conform to the shape of the body surface to which it is applied as compared to a complete soaked and dried sponge which shows a dry cookie structure and is by far less flexible.

The flexibility of the sponge can be measured by any method known to the skilled person. For example, by the three point bending flexural test using a flexural fixture such as GF-54 3-Point Bend Jig; LLOYD instruments Ltd. and a tension and compression testing machines such as LF plus series, LLOYD instruments Ltd, Hampshire, UK. This test measures the tendency of an object to deform along an axis when opposing forces are applied along that axis.

The term "protein or peptide active ingredient" includes any compound made of amino acids and joined together through peptide bonds. The term includes oligopeptides, protein fragments, analogs, fusion proteins and the like. The amino acid chain can comprise additional moieties such as lipids, oligosaccharide chains. The active ingredient may be natural or synthetic. Examples of proteins or peptides active ingredients include, but are not limited to, blood coagulation factors such as thrombin, proteolytic enzyme obtainable from snake venom, fibrinogen, vitamin k-dependent-clotting factors, factor XIII, fibronectin, von Willebrand; RGD peptides; growth factors such as platelet derived growth factors, cartilage inducing factors, osteoid inducing factors, bone growth factors, collagen growth factors; cytokines; interferons; hormones; therapeutic agents such as antimicrobial agents, anti-inflammatories; anti-cancer drugs; chemotherapy agents; analgesics; interleukins; minerals; molecules which stimulate cell migration, adhesion and/or proliferation; enzymes; neurotrophic factors such as nerve growth factor (NGF); ciliary neurotrophic factor (CNTF) and combinations thereof. The active ingredients can be isolated from plasma of human beings or mammals or can be recombinant.

The sponge can be coated with various proteases such as hyaluronidase or collagenase or with various combinations of specific protease inhibitors for treating non healing ulcer or facilitate the re-growth of skin.

The amount of protein or peptide active ingredient in the solution which is applied to the sponge can vary from very low to above saturation. Of course, the actual amount of the active ingredient will depend on, among other things, its intended purpose, its effectiveness, the disease condition, the age and the weight of the patient. According to the invention, a colloidal solution can be applied to the surface of the sponge. It is desirable that the proteins or peptides active ingredients substantially retain their activity following the drying procedure.

The amounts and concentrations of the active ingredient in the layer can be determined empirically by any method known to the skilled person. For example, thrombin activity can be determined directly, by the modified, European Pharmacopeia Assay (0903/1997) procedure, the clotting time is calculated automatically by a clotting machine and the activity is interpolated from a calibration curve prepared using an appropriate thrombin standard, and/or indirectly, by measuring migration length on a slanted surface (or drop test model), or by any other method known to the skilled person.

The liquid comprising the active ingredient can be any liquid carrier. The term "carrier" refers to a diluent, or a vehicle with which the active ingredient is mixed or formulated to facilitate its application to the surface of the sponge. The carrier can be selected from any of the carriers known in the art which are suitable for administering into the body. Non-limiting examples of carriers are: water, sodium chloride solutions such as saline and organic solvents and their mixtures.

In one embodiment of the invention, the active ingredient is thrombin. In such an embodiment, the thrombin can be prepared from initial blood composition. The blood composition can be whole blood or blood fractions, i.e. a product of whole blood such as plasma. Thrombin can be autologous, human including pooled plasma, or of nonhuman source. It is also possible that the thrombin is prepared by recombinant methods. The thrombin can comprises calcium chloride as an additional active ingredient. The concentration of thrombin in the solution can be in the range of from about 2 to about 15,000 IU/ml, in the range from about 2 to about 4,000 IU/ml, or in the range of from about 4,000 to about 10,000 IU/ml. Calcium chloride concentration in the solution can be in the range of from about 2 to about 6.2 mg/ml, or in the range of from about 5.6 to about 6.2 mg/ml, such as in the concentration of 5.88 mg/ml. The thrombin may also comprise excipients. As used herein the terms "excipient" refers to an inert substance which is added to the solution. The excipients can be added into the solution in order to ensure that the active ingredient retains its chemical stability and biological activity upon storage, or for aesthetic reasons e.g. color. Examples of excipients include, but are not limited to, human albumin, mannitol and sodium acetate. The human albumin in the solution can be in the range of from about 2 to about 8 mg/ml. Mannitol can be in the concentration range of from about 15 to about 25 mg/ml. Sodium acetate can be added to the solution in the range of from about 2 to about 3 mg/ml. The thrombin can also comprise carriers such as water for injection.

In another embodiment of the invention, the active ingredient is thrombin which is formulated with L9 buffer solution (20 mM sodium acetate, 40 mM $CaCl_2$, 110 mM NaCl, 0.5% w/w human albumin, 2% w/w mannitol at pH 6.9-7.1).

Haemostatic characteristics of the gelatin sponges prepared by partial soaking with a thrombin solution and drying by using a vacuum oven were tested in the in vivo Rat Kidney Hemorrhage Model as described in the example methods. The results show that the sponges prepared according to the method of the invention and dried in a vacuum oven were efficient in preventing blood loss when applied to a bleeding surface and were more malleable than completely soaked and dried sponges.

Also, the findings show that a ready-to-use gelatin sponge according to the invention which comprise thrombin as the active ingredient is very efficient in preventing blood loss in an in vivo setting. For example, it was found that a sponge prepared according to the invention by using thrombin was at least 3 times more effective in stopping blood loss than the control sponge lacking thrombin. In one embodiment of the invention, thrombin and calcium chloride are the sole active ingredients in the layer of the ready to use sponge. The term "sole active ingredient" means that the specified active ingredient is the only chemically active component required for the function of the product. In another embodiment of the invention, epsilon aminocaproic acid (EACA) is absent from the layer comprising the active ingredient.

Advantageously, the liquid comprising the active ingredient can be applied to the surface of the sponge only once in a single step. This approach eases scale-up of manufactoring procedures. The liquid can be applied by any of the methods known to one of ordinary skill in the art including, but not limited to, physical adsorption, capillary force, spraying, partially soaking, pipetting, pressing the sponge against a roller saturated with a solution comprising the active ingredient, by using a drip on apparatus or an applicator comprising at least one jet or by using a dispenser such as by a spray dispenser or by using the PipeJet™-technology. In any case, the volume of the liquid applied to the sponge during the wetting step should be not more than 5% of the initial volume of the sponge as explained above. In one embodiment of the invention, the liquid is applied by passive capillary force. In another embodiment of the invention, the liquid is applied by pressing the sponge against a roller saturated with a solution comprising the active ingredient. According to the invention any roller having an external surface which contains plurality of hollowed spaces capable of holding liquid on its rolling surface can be used. Such a surface permits an accurate determination of the volume of liquid held per unit area of the roller surface. In one embodiment of the invention, the hollowed spaces are engraved in the external surface of the roller. In another embodiment of the invention, the roller is covered with a porous net. The hollowed spaces can be of any suitable geometry such as diamond, square or rectangle. The net can be of any material that is suitable for use with biological solutions such as polypropylene, polyester. By "suitable" it is meant an inert material which does not interact with the biological solution.

The ability of the hollowed spaces to maintain the liquid can be affected by different means, for example, by the surface tension and the viscosity of the solution and the material of the rollers, i.e. hydrophilic or hydrophobic substances. Typically, the space size to be employed will be determined according to the properties of the solution and the material of the rollers.

It is also possible to use a roller having a smooth surface to which a predetermined amount of liquid is applied circumferentially by suitable technique such as by soaking, dipping or by using a brush or spraying the surface of the roller with the liquid solution.

At least a portion of the external surface of the roller which comes into contact with the surface of the sponge to be coated shall be in contact with a reservoir comprising the liquid solution. The fluid transport mechanisms from the external surface of the roller onto the surface of the sponge may utilize driving forces such as gravity to assist fluid distribution throughout the surface of the sponge. The liquid can be transported onto the surface of the sponge by contacting the external surface of the roller with the surface of the sponge to be coated and moving the external surface of the roller and the surface of the sponge with respect to each other. In one embodiment of the invention, the roller is rolled along the surface of the sponge to be coated. In another embodiment of the invention, the sponge is moved against the surface of the roller.

In one embodiment of the invention, the sponge is fed into an apparatus comprising two counter-rotating rollers: a lower roller and a vertically movable upper roller, two elevated sections capable of adjusting the gap space between the upper and lower roller such as two tuning screws, means for rotating at least one of the rollers such as a motor, and a bath for holding a biological solution as exemplified below. In such an embodiment, the lower roller includes plurality of hollowed spaces and is in contact with a reservoir comprising the liquid solution. The lower roller can be stationary or alternatively can be capable of moving interchangeably.

When using such an apparatus as exemplified below, the liquid applying step can be carried out as follows: the gap space between the rollers is fit to match the thickness of the sponge to be coated. Afterwards, the apparatus is placed on a hard level surface and the leveling of the apparatus is adjusted using a leveling tool. The liquid is applied to the bath and the apparatus is operated. The speed is adjusted to the desired RPM. Generally, the speed should be adjusted to allow application of a volume of liquid which is equal or less than 5% of the initial volume of the sponge. The lower roller runs in the bath comprising the liquid composition, which fills the pours structure of the roller with the coating material. Advantageously, this step is carried out until a liquid equilibrium uptake between the lower roller and the bath is achieved. It is desirable to have a continuous uniform layer of the liquid material over the surface of the lower roller. This can be obtained by using a device which removes excess material from the surface of the roller such as a doctor blade set. This way the liquid can be retained within the porous structure. Then, the sponge is passed between the two rollers and the biological solution is passively deposited onto the bottom side of the substrate by capillary force. During the wetting step the upper roller applies pressure onto the sponge thereby enabling the sponge to be ejected from the apparatus and controlling the liquid uptake capability of the sponge. The sponge is weighed before and after the wetting step and the liquid uptake is calculated by subtracting the weight of the sponge following the wetting step from its weight prior to wetting.

Another roller apparatus which can be used in accordance of the invention is disclosed in U.S. Pat. No. 4,522,057 which content is incorporated herein by reference. The results show that using a roller apparatus to apply the liquid onto the surface of the sponge is advantageous, since by this technique the liquid applied into the sponge can be controlled.

In a further embodiment of the invention, the liquid solution is applied onto the surface of the sponge by using a liquid dispenser. Yet in another embodiment of the invention the liquid solution is applied onto the surface of the sponge by using the PipeJet™-technology. This technology is a valve free method for non-contact dispensing of liquids in the range of a few nanoliter up to several microliter. It has been shown that using a liquid dispenser such as the PipeJet™-technology enables to control the dispensed volume in a defined and an accurate manner throughout the surface of the sponge, consequently resulting in a substantially uniform distribution of the liquid comprising the active ingredient on the surface of the sponge.

Advantageously, the liquid solution is not applied to the surface of the sponge by injection or by any other method which applies mechanical pressure onto the sponge; since application by these methods may result in a deeper penetration of the liquid into the sponge, in a non homogenous distribution of the active ingredient on the surface of the sponge, and/or in considerable deformation of the sponge.

The term "homogenous", as used in this context, denotes that the liquid comprising the active ingredient is substantially uniformly applied throughout the surface of the sponge. Consequently the active ingredient is uniformly dispersed over the surface of the sponge as a thin layer. Advantageously, different regions of the layer which are equal in size have approximately the same biological activity.

An appropriate cross-linked gelatin sponge can be any absorbable sponge product such as: a self manufactured gelatin sponge, e.g. as described in the examples, or by using various commercial sponges such as SPONGOSTAN®, GELITASPON.

When manufacturing the ready to use cross linked gelatin sponge according to the invention, a wetting agent can be incorporated into the gelatin solution prior to foaming, applied to the surface of the cross-linked gelatin sponge prior to the wetting step, or included in the liquid comprising the active ingredient. Such an addition is not required, however. In any case, the volume of the applied liquid to the sponge during the wetting step should be to an extent of equal or less than 5% of the volume of the sponge.

The sponge of the invention can be prepared and provided in a variety of sizes and shapes such as square, polygonal, spherically, conically, cubically, oval, rectangular, or cylindrically, depending on the intended use. For example, the ready to use cross-linked gelatin sponge of the invention can be prepared using the following sponge sizes: 8×3 cm, 10×10×1 cm, 1×1×1 cm, 7×5×1 cm, 2.5×2.5×1 cm.

Another aspect of the invention relates to an improved dry and ready to use cross-linked gelatin sponge comprising a layer of a protein or peptide active ingredient on at least one surface of the sponge. The layer has an average thickness of not more than about 24% of the overall thickness of the ready to use sponge.

The active ingredient in the layer can be any substance suitable for administration to a patient and that induces a desired effect as specified above. In one embodiment of the invention the active ingredient is thrombin. In another embodiment of the invention the active ingredient is thrombin and calcium chloride. Alternative amounts and concentrations of thrombin and calcium chloride may be used. The amounts and concentrations in the layer comprising the active ingredient are preferably selected to optimize the efficacy and functionality of the protein. The thrombin activity in the layer of the ready to use sponge can be in the range of about 1 to about 300 $IU/cm^2$, in the range of about 10 to about 40 $IU/cm^2$, in the range of about 20 to about 40 $IU/cm^2$, or about 35 $IU/cm^2$ thrombin.

In the present context, the term "thrombin" includes prothrombin which is a precursor for thrombin. In the case that prothrombin is used, its concentration in the layer of the ready to use sponge can be a concentration which corresponds a thrombin activity of about 1 to about 300 IU per $cm^2$.

The layer can further comprise excipients and/or carriers as specified above. Examples of excipients include, but are not limited to, human albumin, mannitol and sodium acetate. In one non-limiting example, the liquid carrier is water for injection.

The layer is characterized in that it is stable and is substantially homogenously distributed throughout the surface of the sponge. The stability of the layer can be assessed by using the stability test described above or by any of the method known to the skilled person. In one embodiment of the invention, when the size of the sample is about 1.7 $cm^2$ and the above stability test is carried out the weight loss of the sample can be less than 5%.

It was found according to the invention that the ready to use cross-linked gelatin sponge can be wetted uniformly in the presence of an aqueous solution without the addition of wetting agents. Thus, in one embodiment of the invention the layer of the ready to use cross-linked gelatin sponge does not require a wetting agent to facilitate hydration time of the sponge.

The thickness and the flexibility of the improved sponge according to the invention are substantially similar to that found in the original counterpart non-layered gelatin sponge. A substantially similar sponge may be a sponge which retains at least 75% of the thickness of the original non-layered sponge and a flexibility of at least 80% of the original sponge.

Subject matter of the present invention embraces a sealed package containing a sterile ready to use cross-linked gelatin sponge according to the invention, which enables removal of the patch without contamination. Various materials may be utilized for the package such as aluminum foil pouch and the like.

Any sterilization method known in the art that does not degrade the biological compounds which are sensitive to thermal procedures can be used including, but not limited to, electron beam irradiation, gamma irradiation, ethylene oxide (EtO) sterilization. In one embodiment of the invention, the ready to use sponge and packaging material are sterilized together using, for example, gamma radiation.

The sponge according to the invention can be provided in a kit form comprising any of the above described sponges. The kit can comprise numerous ready to use sponges. The sponges can be contained within a sealed sterile package. In addition the kit can comprise a sterilized surgical instrument for example, scalpel, hemostat and/or instruction for use. The kit can also comprise sterile bandages, sterile pads, gauze and/or disinfectant. The kit can further comprise a sterile saline solution.

A ready to use sponge or kit according to the invention can be advantageously used in surgery such as in neurosurgery; brain surgery; reconstructive and cosmetic surgery of tissues, such as cartilage, nerve and bone regeneration. The ready to use sponge or kit can be used also for arresting bleeding, preventing adhesions and/or for repairing and/or treating injured tissue.

In one embodiment of the invention, the sponge is coated with a haemostatic agent. The term "haemostatic agent", as used herein, refers to the ability of the agent to control, reduce or stop capillary, venous, or arteriole bleeding, including severe or brisk bleeding, within an effective time, as recognized by those skilled in the art. The bleeding can occur as a result of surgical procedures, haemostatic disorder or in other situations, for example, in patients with coagulopathies or who are receiving heparin or anticoagulants.

As used herein "severe or brisk bleeding" refers to cases of bleeding where high volumes and high rate of bleeding occurs. Examples of sever and brisk bleeding include, but not limited to, bleeding due to arterial puncture, liver resection, kidney resection, hemophiliacs and patient receiving anticoagulant medication and the like.

Examples of hemostatic agents include, but not limited to, prothrombin, thrombin, fibrin, fibronectin, Factor X/Xa, Factor VII/VIIa, Factor IX/IXa, Factor XI/XIa, Factor XII/XIIa, factor XIII, factor VIII, vitronectin, tissue factor, proteolytic enzyme obtainable from snake venom such as batroxobin, von Willebrand Factor, plasminogen activator inhibitor, platelet activating agents, synthetic peptides having hemostatic activity, derivatives of the above and any combination thereof.

When using the sponge as a haemostatic product, additional substances which encourage the formation of the clot can be included in the layer comprising the active ingredient, such as calcium chloride.

The ready to use sponge can be soaked in a sterile saline solution prior to use, e.g. when the body fluids are insufficient to provide adequate hydration of the sponge. Alternatively, the sponge can be applied without first soaking in saline solution and the haemostatic agent is activated by the body fluids.

The ready to use sponge can be applied onto the desired site and held under pressure for a period of time sufficient for clotting to occur at the interface between the sponge and the application site and for bleeding to be substantially ceased.

In another embodiment of the invention, the active ingredient is an anti-adhesive agent. In such an embodiment, the ready to use sponge can be used in the prevention of adhesions. Adhesion is an undesired side-effect in which body tissues that are normally separated grow together. This undesirable side-effect can occur as a result of surgical procedures or non-surgical insults such as endometriosis, infection, trauma, chemotherapy, radiation and cancer. Typically, anti-adhesive agents refer to agents that are capable of forming a physical barrier (coating) which separates between adjacent tissues at the surgical site and therefore prevent and/or reduce formation of postoperative adhesions.

The sponge can further comprise one or more protein or peptide active ingredient and serve as a drug delivery system.

The term "drug delivery system" refers to delivery of active proteins or peptides which are incorporated into the sponge allowing a controlled delivery of the protein or peptide in a specific tissue in vivo.

The sponge made according to the invention has at least one of the following advantages: original flexibility, texture, intactness of porous structure, an active ingredient that is highly concentrated as a thin layer at the interface to be contacted with the wound, a layer which is stable, and robustness of performance.

The disclosure of ranges in the description of the invention is easily understood by the skilled person. It means the disclosure of continuous values and figures between the limits of the ranges, including the limiting figures and values with all combinations of intermediate sub ranges.

The disclosure of applications, patents and publications, cited above or below, is hereby incorporated by reference.

The following examples are illustrative but not limiting.

EXAMPLES

Methods

Lyophilization Drying Procedure. The lyophilization procedure was carried out as follows using the CHRIST, EPSILON 2-8D Freeze Dryer: The shelves temperature was lowered to −45° C. for 2 hours. Afterwards, the temperature was lowered to −50° C. for an additional 30 minutes. Then, the shelves were kept at −50° C. for a period of 5 hours. This step was followed by sublimation at −15° C. and 0.14 mbar for up to 24 hours. After that the shelves temperature was increased to +25° C., pressure was reduced to 0.02 mbar and a secondary drying was carried out for up to 24 hours.

Vacuum Drying Procedure. Vacuum drying procedure was done in an oven (ShelLaB Model 1430-2E) set to room temperature at a pressure of 0.1 bars or less for 3 to 4 hours.

Production of Gelatin Sponge (in house sponge). 30 g gelatin flakes (PB Gelatins; Pharmaceutical gelatin, Type A from pig skin, 250 Bloom, 8 mesh; Cat. No. 1154) were added to 500 ml distilled water. The dispersion was heated to 60° C. until the gelatin was completely dissolved. The solution (6% w/v) was then cooled to 50° C. and transferred to a mixer bowl (KitchenAid Heavy Duty Model KSM150) where it was whipped at speed 6 for about 2 minutes until stable foam was formed with a 6-8 fold higher volume compared to the initial volume of the gelatin solution. The foam was poured into a metal mold (21×30 cm with a depth of 1.5 cm). In order to harden the foam, the mold was placed at 4° C. for 1 hour. Afterwards, the mold was transferred to a lyophilizer with pre-cooled shelves (4° C.). The lyophilization drying procedure was carried out as described above. Following the drying procedure, the dry sponge was cross-linked at 160° C. for 3 hours at atmospheric pressure.

Thrombin Release from the Sponges. The sponges [2.5× 2.5×1 (thickness) cm] were immersed in 10 ml buffer (0.4% Tri-sodium citrate dehydrate, 154 mM NaCl and 1% BSA) inside a 50 ml polypropylene tube. The tube was placed on a roller at roomtemperature.

Thrombin release from the sponges was measured by determining the recovered thrombin activity in the buffer at the various time points. Thrombin clotting activity was measured according to the following modified, European Pharmacopeia Assay (0903/1997), procedure. Briefly, each standard solution of thrombin (4, 6, 8 and 10 IU/ml; Omrix IL; prepared as described in U.S. Pat. No. 5,143,838 and in EP patent 378,798) was incubated for 2 minutes at 30° C. Then 40 µl thrombin solution of each standard solution was mixed with 160 µl fibrinogen solution (0.1%; Enzyme research Laboratories; cat No FIB1) and clotting time was measured (Haemostaisi analyser: Diagnostica Stago; Model Start). A calibration curve of log clotting times vs. log thrombin concentration was plotted. Then, 0.3 ml samples were taken out from the tube out of which 40 µl were used for the measurement (the same amount of buffer was added back to replace the sample volume). The measurements were carried out in duplicates in the following time points 2, 5, 10, 15, 30, 45 and 60 min after the beginning of the experiment. Thrombin activity in each sample was determined by the clotting time obtained (calculated automatically by a clotting machine, interpolated from the calibration curve and multiplied by the dilution factor).

Rat kidney hemorrhage model. Sprague Dawley albino rats, weighing 350-500 g were housed in an authorized facility according to the current ethical requirements. The health of each animal was ascertained and only overtly healthy animals were used for testing. Following receipt, the animals were subjected to an acclimation period of at least 5 days. The animals were provided ad libitum a commercial rodent diet and free access to drinking water. The animal was anesthetized with an intraperitoneal injection of Pental (30-50 mg/kg). Afterwards, the animal's fur was shaved on the left flank for the paralumbar laparotomy. The shaved site was wiped with alcohol. To maintain a temperature of 38-40° C., the rat was placed on a plastic cover deck on top of a water bath preheated to 40° C. A thermo probe was inserted into the animal's rectum and the body temperature was monitored. The animal was positioned laterally and Sodium Heparin (2000 IU/Kg) was injected intravenously through the tail vein. A left paralumbar incision was made from the left hip to the twelfth rib, and the left kidney was exposed and separated from the perirenal fat. The rat was re-positioned to dorsal recumbence and allowed to stabilize for a period of five minutes or until the body temperature was utmost 39° C. The renal vessels were occluded with a soft vascular clamp and a gauze pad was tucked into the dorsal edge of the incision, between the exteriorized kidney and the incised abdominal wall, to absorb any blood or fluid shedding from the incision or from the abdominal cavity behind the kidney. A piece of transparent pre-cut plastic was placed on top of the gauze pad in order to direct the blood flow from the kidney into the pad. Another one or two squares of gauze were laid at the base of the plastic platform and the renal vessels were occluded with a soft vascular clamp. A sagital heminephrectomy was performed and the entire distal half of the kidney was removed perpendicular to the renal vessels. The cut surface of the removed section of the kidney was blotted three times on a piece of filter paper to measure the surface area of the excision. Each of the three kidney blots were traced, to aid in surface area determination. The cut surface of the remaining kidney was blotted dry. Gelatin sponge was applied onto the cut surface of the kidney for 1 minute under pressure before releasing the renal clamp. The kidney was observed for incidence of bleeding for a period of one hour. When bleeding through the sponge occurred, the area of bleeding was gently blotted with gauze. Removal of the gelatin sponge from the bleeding surface resulted in resumption of bleeding, demonstrating that the cessation of bleeding was due to the gelatin sponge application. Renal blood loss was assessed by weighing the blood-soaked pads. Surviving animals were euthanized by $CO_2$ asphyxiation.

Stability assessment of the protein layer. The stability assessment measures the friability of the protein layer from the sponge. A sample of about 1.7 cm² was cut from the ready to use cross-linked gelatin sponge using a die-cutter and its weight was determined. The sample was then placed within a borosilicate glass scintillation vial (Fisher Scientific; cat No 03-337-4) while the coated surface was facing up and the vial was cupped. A support stand having an extension clamp, capable of holding a plastic tube (48-inch long and 1.625 inches in diameter), was placed on a hard level surface. The plastic tube was inserted vertically into the clamps, the clamps were tightened and a solid silicone stopper (Fisher Scientific; cat No 09-704-1P) was placed in the bottom of the plastic tube. A plastic block was placed underneath the silicone stopper to prevent it from being expelled during the measurements. Afterwards, the vial containing the sample was dropped from the top of the plastic tube with the cap side up. Each drop was carried out from the same point in order to exdude variability and ensure standardization. After the sample has been drooped 4 times, the sample was weighed. The powder loss was calculated by subtracting the post-drop weight of the sample from the pre-drop weight of the sample. The percentage of weight reduction of the sample was calculated according to the following formula:

$$\frac{\text{Powder loss}}{\text{Pre-drop weight}} * 100$$

A weight reduction of less than 5% is regarded as a stable layer which does not flake off from the surface of the sponge.

Preparation of 8000 and 4000 IU/ml thrombin solutions.

Concentration and diafiltration of the 1000 IU/ml thrombin solution (Omrix, IL; prepared as described in prepared as described in U.S. Pat. No. 5,143,838 and in EP patent 378,798) was carried out using 10K Omega™ Ultrafiltration Membrane Disc Filters (SER No. 39182101) thereby obtaining a 8000 IU/ml thrombin solution. Thrombin solution 4000 IU/ml was prepared by dilution of the 8000 IU/ml solution with L9 buffer solution (1:1 ratio). Concentration and diafiltration of the L9 buffer solution was carried out using the above indicated filters.

The three point bending flexural test. This test provides values for the modulus of elasticity which measures the tendency of an object to deform along an axis when opposing forces are applied along that axis. The measurements were carried out using a flexural fixture (GF-54 3-Point Bend Jig; LLOYD instruments Ltd). Once the bending hubs of the fixture were adjusted to a span of 40 mm, the specimen was placed on them and compressive force was applied on the specimen throughout the duration of the bending test (LF plus series, LLOYD instruments Ltd, Hampshire, UK). The extension rate was set to 15 mm/min. The bending test was carried out until rupture of the specimen.

Example 1

The Relationship Between the Liquid Uptake into the Sponge and the Thickness and Appearance of the Gelatin Sponge after Vacuum Drying Procedure This experiment was aimed to determine the influence of the liquid uptake into the sponge on the sponge thickness and appearance following drying. NP40, a nonionic surfactant, was added into the liquid formulation to alter the liquid uptake into the sponge. For this purpose, 7×5×1 (thickness) cm SPONGOSTAN® sponges (distributed by Johnson &

Johnson; cat No MS 0002) were cut to a size of 2.5×2.5×1 cm. These sponges, weighing 80-90 mg, were placed in a plastic tray [3×3×0.2 (depth) cm] containing various liquid formulations and volumes for 3 minutes. The study design is listed in Table 1 below. Hydration occurred as a result of capillary action. The liquid uptake into the sponges was monitored gravimetrically by weighing the sponges before and after the wetting procedure wherein 1 mg was considered as 1 µl. Afterwards, the sponges were dried in a vacuum oven as described above and their thickness was measured. The results are specified in Table 1 below.

TABLE 1

The Liquid Uptake into the Sponge and the Thickness of the Sponge Following Drying Procedure in the Different Formulations.

| Sponge No. | Liquid volume in the tray (µl) | Liquid | Liquid uptake into sponge (mg) | Thickness (mm) |
|---|---|---|---|---|
| 1 | 500 | saline | 118.4 | 9 |
| 2 | 500 | distilled water + 0.1% NP40 | 457.8 | 3.7 |
| 3 | 200 | L9 + saline + 0.5% MB | 44 | 9 |
| 4 | 200 | L9 + saline+ + 0.01% NP40 + 0.5% MB | 163.9 | 7.2 |
| 5 | 600 | L9 + saline + 0.5% MB | 161.2 | 8.25 |
| 6 | 600 | L9 + saline + 0.5% MB | 164.7 | 8.25 |
| 7 | 600 | L9 + saline + 0.01% NP40 + 0.5% MB | 567.8 | 4.75 |

*L9 composition - 20 mM Sodium Acetate, 40 mM $CaCl_2$, 110 mM NaCl, 0.5% w/w human albumin, and 2% w/w Mannitol; pH 6.9-7.1.
**MB - Methylene Blue (Spectrum Chemicals and Laboratory Products; cat. No. ME141, USP - 25 g).

A. The Effect of the Liquid Uptake into the Sponge on the Thickness of the Sponge after Vacuum Drying.

Sponges No. 1 and 2 were partially soaked in 500 µl saline and distilled water+0.1% NP40, respectively. Measurements of the sponge's liquid uptake reveled that partial soaking in fluids containing distilled water+0.1% NP40 resulted in higher liquid absorption and in a significant decrease in the sponge's thickness upon vacuum drying as compared to saline-soaked gelatin sponge (sponge No. 2 and No. 1; 457.8 mg liquid uptake and 3.7 mm thickness vs. 118.4 mg and 9 mm, respectively). The liquid uptake and the sponge's thickness are listed in Table 1.

Figure 1B:
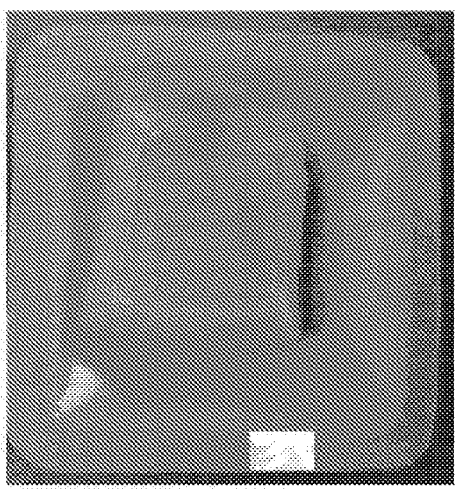
Figure 1C:
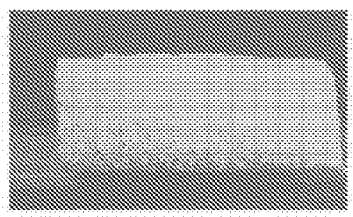
Figure 1D:
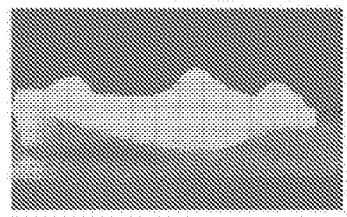

FIGS. 1A-B show a top view of a sponge partially soaked in saline (A; sponge No. 1) as compared to a sponge partially soaked in distilled water+0.1% NP40 (B; sponge No. 2) following the drying procedure. The results show that sponge B is distorted and shrunk, especially on the upper side where it absorbed liquid. In a sided view of the sponges it is evident that sponge 2 is thinner than sponge 1 (FIGS. 1D and C, respectively). The sponge thickness following drying was shown to be reversibly proportional to the liquid uptake.

Figure 2A:
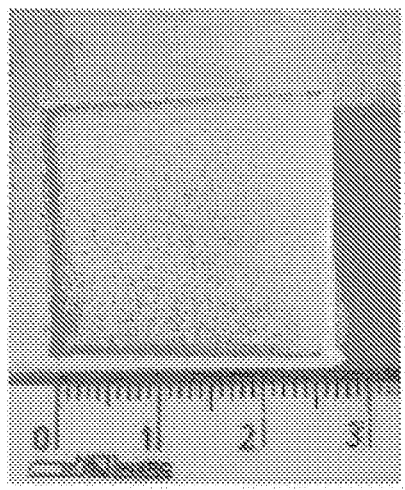
FIGS. 2A-D: show a top view of gelatin sponges No. 6 (A) and No. 7 (B) partially soaked in 600 μl L9+saline+0.5% Methylene Blue (MB) and L9+saline+0.01% NP40+0.5% MB, respectively. A sided view of the sponges is shown in C and D (sponge No. 6 and 7, respectively).
Figure 2B:
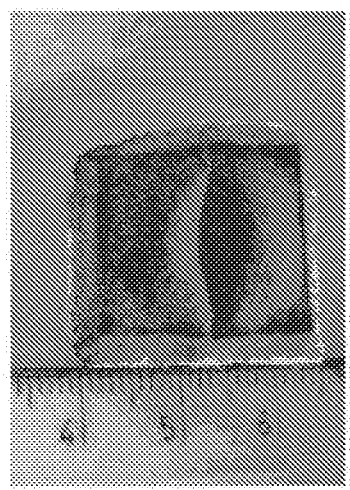
Figure 2C:
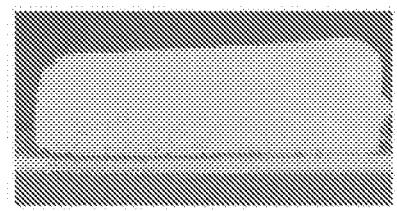
Figure 2D:
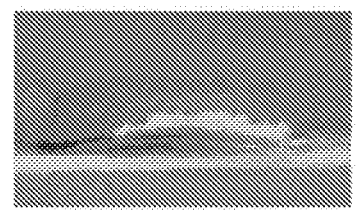

When comparing sponge 6 and 7 [600 µl of L9+saline+ 0.5% Methylene Blue (MB) and 600 µl L9+saline+0.01% NP40+0.5% MB, respectively] the results show that sponge No. 7 absorbed more than 3 folds liquid compared to sponge No. 6 (567.8 vs. 164.7 mg, respectively). As shown in the previous set of experiments, the high liquid uptake of sponge 7 resulted in a significant reduction in the sponge thickness upon vacuum drying (4.75 as compared to 8.25 mm of sponge 6). A top view of sponges 6 and 7 (FIGS. 2A-B, respectively) shows that sponge 7 is shrunken as compared to sponge 6. A side view shows that sponge 7 is thinner and distorted as compared to sponge 6 (FIGS. 2D and C, respectively). This is as a result of the high liquid uptake of the sponge which resulted in collapse of the sponge during drying.

Also, comparison of sponge No. 3 and 4 which were partially soaked in 200 µl L9+saline+0.5% MB and 200 µl L9+saline+0.01% NP40+0.5% MB, respectively, shows an increase the liquid uptake as a result of the presence of surfactant.

The above results indicate that incorporation of surfactant, e.g. NP40, to the solution facilitates or enhances the hydration time of the sponge. Inclusion of surfactant leads to a decrease of surface tension in the liquid composition, which results in an increase in the liquid uptake into the sponge. It is seen that this leads to a significant reduction in the sponge thickness upon vacuum drying. Thus, when using a surfactantcontaining composition the soak time should be decreased as compared to the hydration time of the same composition without such an agent in order to avoid drying shrinkage and deformation of the sponge.

B. The Effect of the Liquid Penetration Depth into the Sponge during Wetting on the Thickness of the Sponge Following the Drying Step.

In another set of experiments SPONGOSTAN® sponges were placed in a tray (the dimensions of the sponges and the tray are described above) containing 200 or 600 µl L9+saline+0.5% MB (sponges 3 and 5, respectively).

Figure 3A:
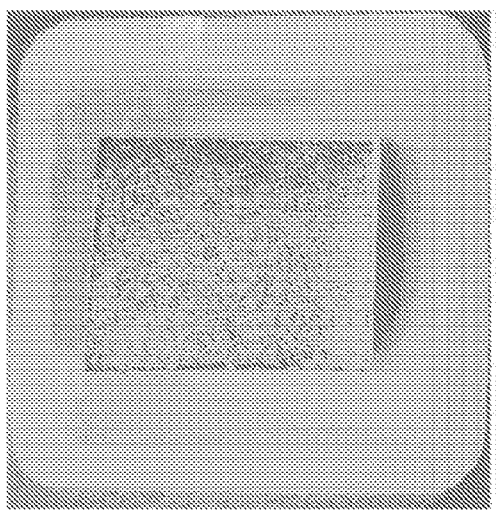
FIGS. 3A-D: show a top view of gelatin sponges No. 3 (A) and No. 5 (B) partially soaked in 200 or 600 μl L9+saline+0.5% MB, respectively. A sided view of sponges 3 and 5 is shown in FIGS. 3C and D, respectively.
Figure 3B:
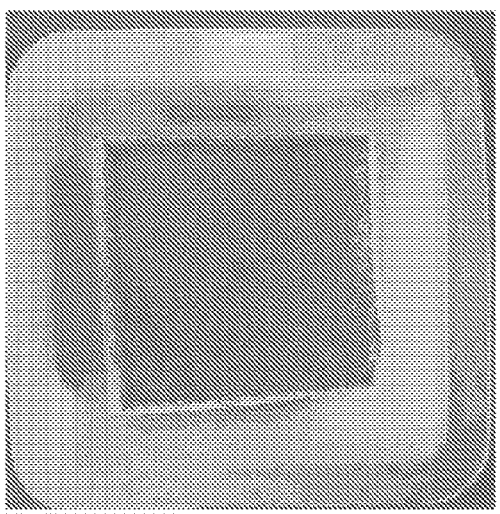

The results show that sponge 5 absorbed about 3.5 times more liquid as compared to sponge 3 (161.2 and 44 mg uptake, respectively). The high liquid absorbance of sponge 5 resulted in an intense coloring of the sponge as compared to sponge 3 (FIGS. 3A-B show a top view of sponges 3 and 5, respectively).

Figure 3C:
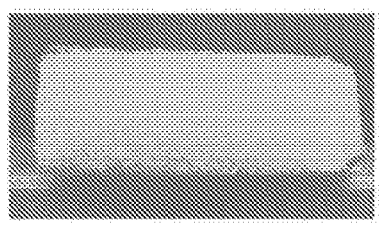
Figure 3D:
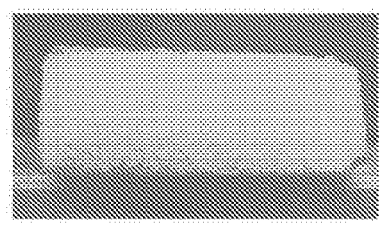

FIG. 3C-D show a side view of sponges 3 and 5, respectively. The above shown results indicate that the volume present in the tray during soaking may affect the liquid uptake into the sponge. Since the liquid penetration depth was relatively low (0.704 and 2.57% of the initial height, for sponges No. 3 and 5, respectively), minimal collapse occurred during vacuum drying in both sponges following the drying step (9 and 8.25 mm, respectively).

Example 2

The Effect of Ethanol on the Liquid Uptake into the Gelatin Sponge

The above example shows that the liquid uptake into the sponge by capillary action is affected by the type of liquid (e.g. incorporation of surfactant). It was also seen that an increased liquid uptake leads to a significant reduction in the drying shrinkage. The following example was carried out in order to further explore the effect of inclusion of surfactant into the wetting composition. Ethanol and GELITASPON (Gelita Medical; cat. No. GS010 Standard 10; size 80×50× 10 mm) were used in these experiments. The sponges were cut to a size of 2.5×2.5×1 cm and placed in a plastic tray [3×3×0.2 cm (depth)] containing various volumes of L9+0.1 M NaCl with or without 20% ethanol. The sponges were incubated for 15 minutes and weighed. The study design is specified in Table 2 below.

TABLE 2

Constitution of Test Groups.

| Liquid volume (µl) | Liquid |
|---|---|
| 250 | L9 + NaCl 0.1 M |
| 250 | L9 + NaCl 0.1 M + 20% ethanol |

TABLE 2-continued

Constitution of Test Groups.

| Liquid volume (μl) | Liquid |
|---|---|
| 400 | L9 + NaCl 0.1 M |
| 400 | L9 + NaCl 0.1 M + 20% ethanol |
| 550 | L9 + NaCl 0.1 M |
| 550 | L9 + NaCl 0.1 M + 20% ethanol |
| 700 | L9 + NaCl 0.1 M |
| 700 | L9 + NaCl 0.1 M + 20% ethanol |

Figure 4:
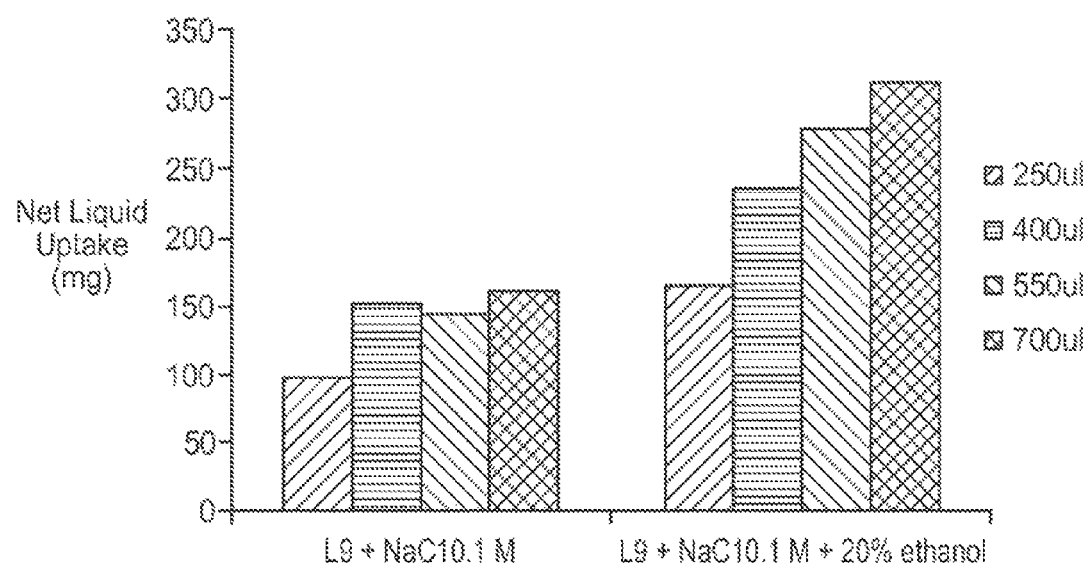
FIG. 4: shows the effect of ethanol on the liquid uptake of GELITASPON, a commercial gelatin sponge, in increasing volumes of L9 (20 mM Sodium Acetate, 40 mM $CaCl_2$, 110 mM NaCl, 0.5% w/w human albumin, 2% w/w Mannitol; pH 6.9-7.1)+0.1 M NaCl.

The results summarized in FIG. 4 corroborate the previous results and show that incorporation of surfactant such as 20% ethanol, leads to modification of the liquid uptake capability of the sponge.

Example 3

The Effect of Surfactant on Thrombin Clotting Activity

The Present Example was Aimed to Determine the Effect of Surfactant Addition on thrombin activity. For this purpose, 0.8 ml thrombin solution (1000 IU/ml; Omrix IL) was mixed with 0.2 ml 95% ethanol. The mixture was incubated at room temperature up to 60 minutes and thrombin activity was measured every 15 minutes. In the control group distilled water was used instead of ethanol. The recovered thrombin activity was measured according to the modified, European Pharmacopeia Assay (0903/1997) procedure specified above in the method section. Table 3 summarizes the recovered thrombin activity in the formulation at the various time points.

TABLE 3

Recovered Thrombin Activity at the Various Time Points.

| Formulation | Time (min) | Thrombin Activity (IU/ml) | Recovered activity (%) |
|---|---|---|---|
| Thrombin + Ethanol | 15 | 677.6 | 83.34 |
|  | 30 | 677.6 | 83.34 |
|  | 45 | 635.2 | 78.13 |
|  | 60 | 645.6 | 79.4 |
| Control | 60 | 645.6 | 79.4 |

The recovered activity in the formulation containing ethanol was similar to the recovered activity of the control group. These findings suggest that 20% ethanol does not affect thrombin clotting activity.

Example 4

The Kinetics of Liquid Absorption by Capillary Action into Various Sponges

This example illustrates the kinetics of liquid absorption into the sponge. The absorption was carried out as a result of capillary action. The experiment was conducted in two sponges of different origin: SPONGOSTAN® (80-90 mg) or in-house sponges (manufactured in Omrix IL as described above). The sponges were placed in a plastic tray (3×3×0.2 cm) which contained 400 μl L9 buffer+0.1 M NaCl. In addition, SPONGOSTAN® sponges were placed in another formulation which contained 400 μl L9 buffer+0.1 M NaCl+ 0.02% Tween 20. Liquid absorption was monitored by weighing the sponges at various time points.

Figure 5:
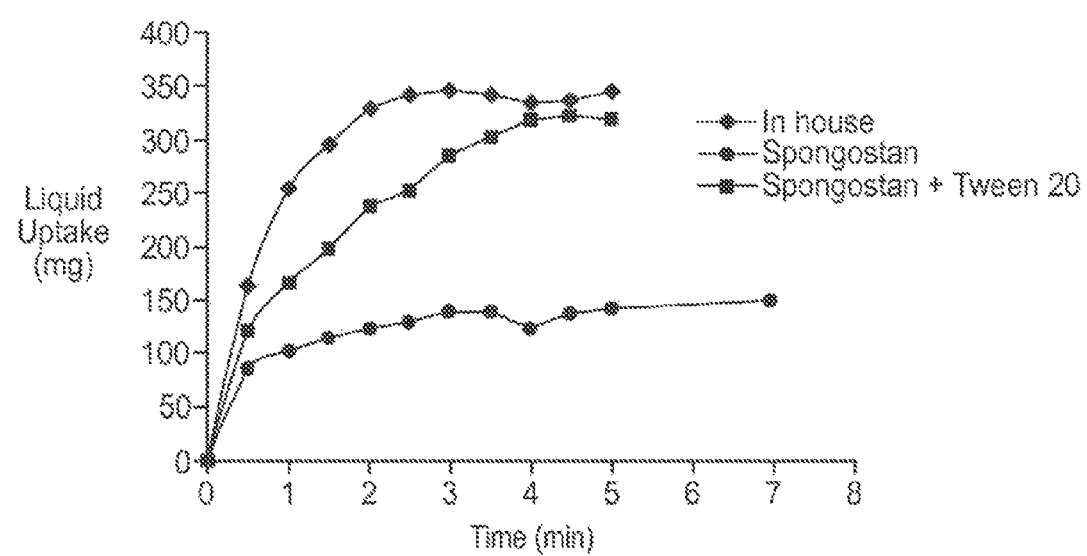
FIG. 5: shows the kinetics of liquid absorption by capillary action into SPONGOSTAN® or in-house gelatin sponges (manufactured in Omrix IL) and the effect of surfactant on the liquid uptake into the sponge.

The results demonstrate that supplementation of the formulation with 0.02% Tween 20 significantly decreased the hydration time required to wet the sponge and increased the liquid uptake capability of the SPONGOSTAN® sponges. Moreover, it is indicated that the in-house sponges absorbed liquid more rapidly compared to the SPONGOSTAN® sponges (FIG. 5).

Example 5

Figure 6:
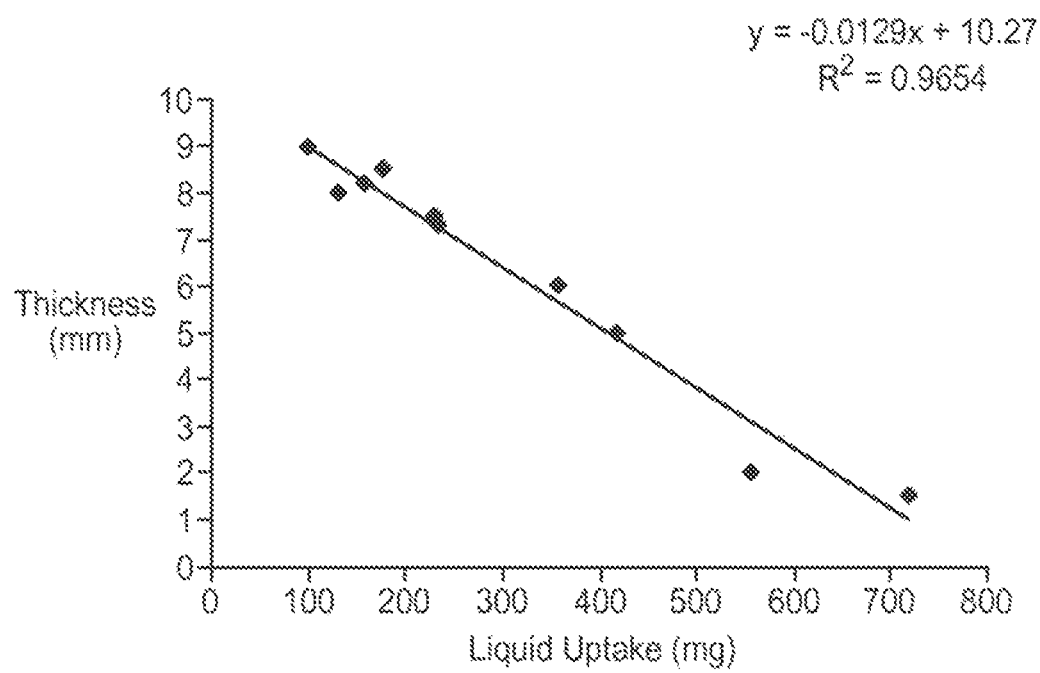
FIG. 6: shows the thickness of the vacuum dried SPONGOSTAN® gelatin sponges plotted as a function of the liquid uptake of the sponge prior to drying.

The Effect of the Liquid Uptake into the Sponge on the Sponge's Thickness after Vacuum Drying It was shown that an increase in the liquid uptake of the sponge lead to a decrease in the sponge thickness upon vacuum drying. These results were verified in the following set of experiments. 2.5×2.5×1 cm SPONGOSTAN® sponges [cut from 5×7×1 cm] were placed in a tray [3×3×0.2 cm] containing various liquid volumes of L9+0.1 M NaCl for 3 minutes. Following the wetting step the sponges were dried in a vacuum oven as specified above in the method section. The liquid volumes in the tray, the dried sponge weight, the liquid uptake and the thickness of the vacuum dried sponges are specified in Table 4 below. FIG. 6 shows the sponge thickness following the vacuum drying procedure plotted against the liquid uptake of the sponge. The results confirm the previous results and show that vacuum drying procedure results in collapse of the excessively wetted sponge. Thus, it is particularly advantageous to apply a small volume of liquid comprising a protein or peptide active ingredient to one surface of the sponge. Using a small volume of liquid for application of the active ingredient, results in a sponge having a thin layer of protein or an active ingredient on that surface; and the original characteristics of the sponge (height, texture and appearance) are substantially retained.

Example 6

Figure 7:
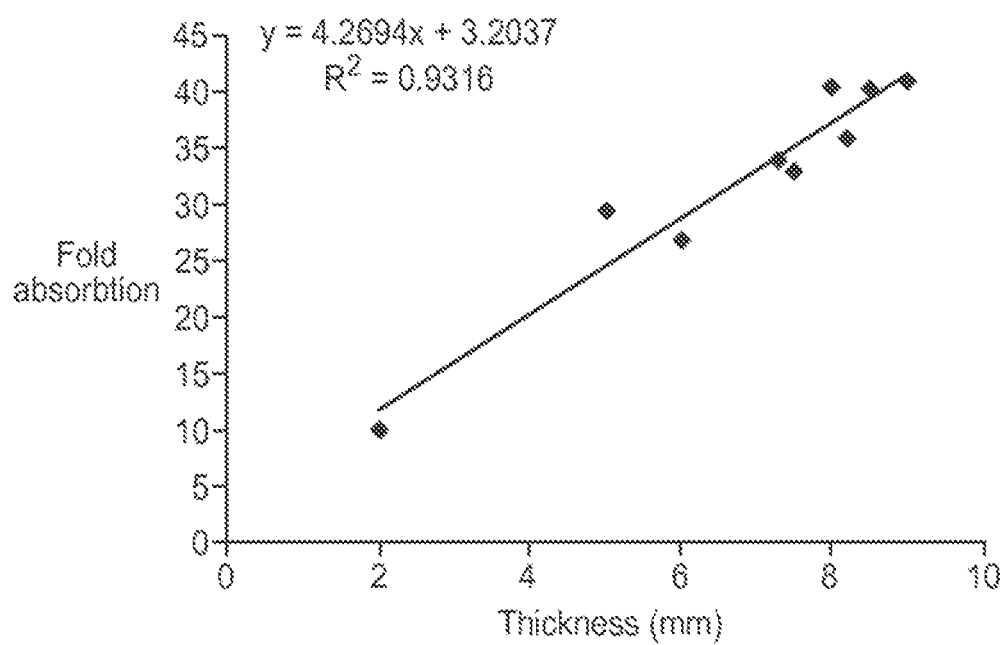
FIG. 7: shows the SPONGOSTAN® gelatin sponges water fold absorption plotted as a function of the thickness of the vacuum dried sponges.

The Effect of the Sponge Thickness on the Water Absorption Ability of the Sponge Following Drying In order to check the effect of the thickness of the sponge following the drying step on its liquid absorption ability, the above mentioned vacuum-dried sponges (from Example 5) were immersed into distilled water for 2 minutes according to the US Pharmacopeia (USP). The sponges were weighed before and after the immersion procedure. The thickness of the sponges, the vacuum dried sponge's weight, the water absorption of the final product, and the water absorption ability of the sponges are listed in Table 4 below. The water absorption ability of the sponge was calculated according to the following formula: (Net water absorption of final product—dry weight after vacuum)/dry weight after vacuum. The sponge fold absorption plotted against the thickness is shown in FIG. 7. The results indicate that the ability of the sponge to absorb fluids is directly proportional to the thickness of the sponge following the vacuum drying procedure, i.e., thin sponges absorb less fluid than thick sponges.

According to the US Pharmacopeia absorbable gelatin sponges should absorb not less than 35 times their weight of water. In order to meet the pharmacopeia demand, SPONGOSTAN® sponges should retain a thickness of equal or more than 7.44 mm, i.e. these sponges should loss not more than 25% from their initial height during the drying procedure. Moreover, in order to obtain a thickness of equal or more than 7.44 mm the liquid uptake of SPONGOSTAN® sponges should be equal or less than 219 μl (according to example 5; FIG. 6). Calculation of the liquid uptake into the sponge show that in order to retain its original structure and avoid deformation which may occur following the drying the liquid uptake into the sponge may be equal or less than 3.5% of the volume of the sponge prior the drying step.

TABLE 4

The Effect of the Liquid Uptake on the Sponge Thickness after Vacuum Drying and on the Water Absorption Ability of the Vacuum-Dried-Sponges.

| Liquid Volume in the Tray (μl) | Dry Sponge Weight (mg) | Liquid Uptake (mg) | Thickness after Vacuum (mm) | Dry Weight after Vacuum (mg) | Net Water absorption of final product (mg) | Water Absorption ability* |
|---|---|---|---|---|---|---|
| 400 | 87.7 | 99.4 | 9 | 95.1 | 3892.1 | 41 |
| 250 | 93 | 156.4 | 8.2 | 101.2 | 3665.9 | 36 |
| 400 | 90.7 | 233 | 7.3 | 100.5 | 3450.6 | 34 |
| 400 | 87.1 | 229.3 | 7.5 | 97.2 | 3208.6 | 33 |
| 550 | 93.3 | 415.6 | 5 | 112 | 3306.7 | 29.5 |
| 550 | 92.4 | 355.5 | 6 | 111.7 | 3032.1 | 27 |
| 750 | 93.8 | 719.4 | 1.5 | 145.3 | 2739.6 | 18.9 |
| 700 | 84.2 | 555.1 | 2 | 130.4 | 130.4 | 10 |
| 400 | 79.4 | 131.4 | 8 | 8 | 3369.2 | 40.5 |
| 400 | 80 | 176.6 | 8.5 | 87.8 | 3567 | 40.4 |

*The water absorption ability of the sponge was calculated as follows (Net water absorption of final product - dry weight after vacuum)/dry weight after vacuum.

Example 7

Comparison Between Lyophilization and Vacuum Drying Procedure on the Thickness of the Sponge It was shown in the previous examples that vacuum drying procedure results in shrinkage of the wetted sponge. The following example was carried out to confirm the above results and to examine the effect of both lyophilization and vacuum drying procedures on the thickness of the sponge. The experiment was carried out using two different gelatin sponges, a commercial sponge (5×7×1 cm SPONGOSTAN® sponge) and an in-house sponge (manufactured as described above).

Both sponges were cut to 2.5×2.5×1 cm, weighing 80-90 mg, and placed in a plastic tray (3×3×0.2 cm) containing increasing volumes of L9+0.1 M NaCl for 3 minutes. The sponge's weight after the wetting step was measured and the net liquid uptake was calculated.

Afterwards, SPONGOSTAN® was dried either in a vacuum oven or in lyophilization (as described above) and the in house sponge was dried by a vacuum oven. The thickness of the sponges was measured following the drying procedure.

Figure 8:
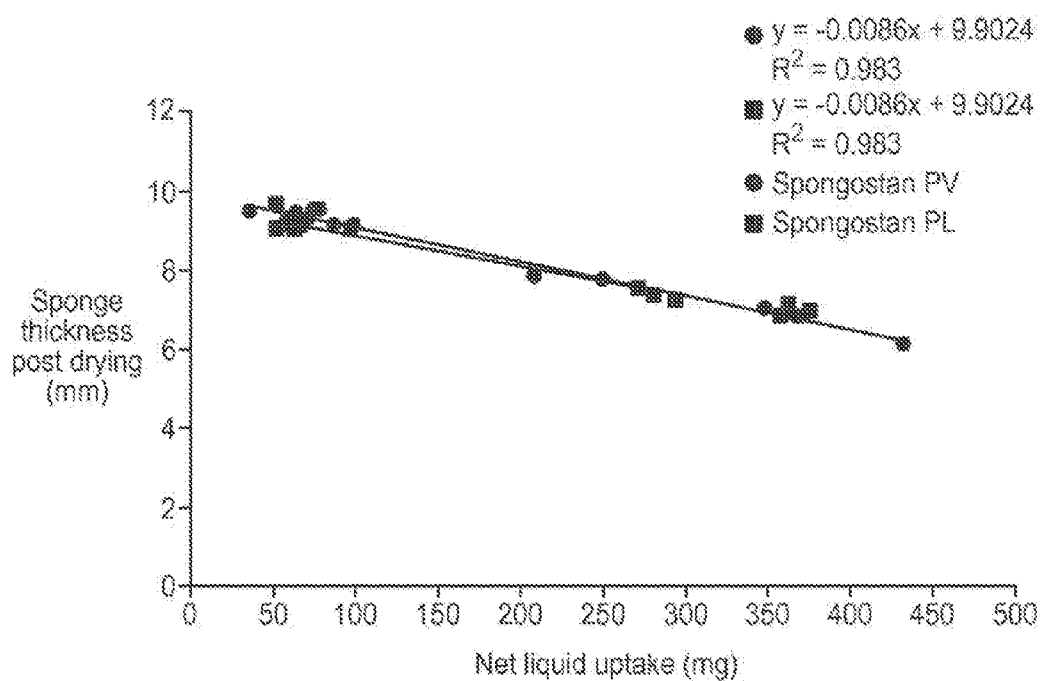
FIG. 8: shows the inverse relationship between the thickness of the SPONGOSTAN® sponges after the drying procedure and the net liquid uptake of the sponge prior to drying procedure. PV—partially soaked sponges followed by vacuum drying; PL—partially soaked sponges followed by lyophilization drying procedure.

FIG. 8 shows the inverse relationship between the thickness of the commercial sponge (SPONGOSTAN®) after the drying procedure and the net liquid uptake during the soaking step. PV—partially soaked sponges followed by vacuum drying; PL—partially soaked sponges followed by lyophilization drying procedure.

Figure 9A:
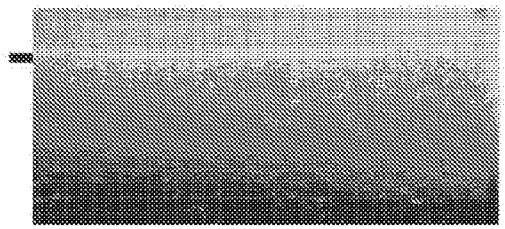
FIGS. 9A-D: show the thickness of the applied active ingredient layer within the vacuum-dried gelatin sponges (A, C) and the lyophilized-dried gelatin sponges (B, D).
Figure 9B:
Figure 9C:
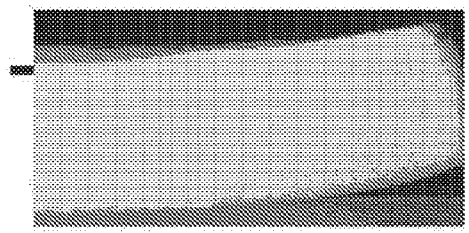
Figure 9D:
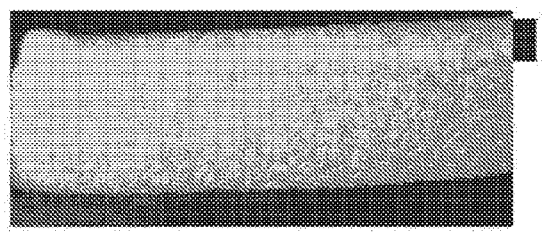

The results show that an increase in the net liquid uptake resulted in a decrease in the thickness of the sponge following the drying procedure in a similar extent in both lyophilization and vacuum drying procedure. However, when comparing the thickness of the layer of the applied active ingredient, the results show that drying in vacuum (FIG. 9A, C) results in a thinner layer as compared to lyophilization drying procedure (FIG. 9B, D). The dried top layer of the vacuum-dried sponge was 5.8-8.3% of the overall thickness of the dried sponge as compared to 12.5-24% in the lyophilized-dried sponge. The thickness layer of the applied material is marked with a black square at the top of each Figure.

Figure 10:
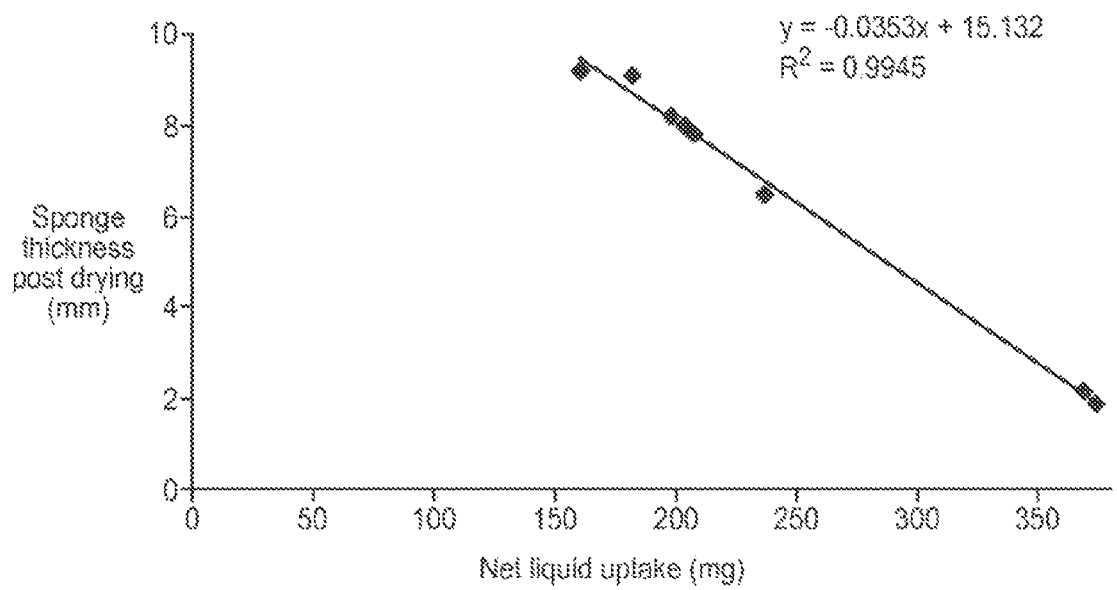
FIG. 10: shows the relationship between the net liquid uptake of the in-house sponge and the sponge thickness after drying.

The results of the relationship between the net liquid uptake of the sponge during the soaking step and the sponge thickness after the drying of the in-house sponge are presented in FIG. 10. These results are in line with the previous results which indicate that there is an inverse relationship between the liquid uptake during the soaking step and the sponge thickness following the drying procedure, i.e. the drying step leads to shrinkage of the excessively wetted sponge. These results emphasize the advantage in applying the liquid composition in a very thin layer.

Example 8

Release of the Active Ingredient from Different Gelatin Sponges

The following example was preformed in order to determine the release of the active material from the gelatin sponge and to assess the in-vivo performance of the sponge. For this purpose, 2.5×2.5×1 cm SPONGOSTAN® gelatin sponges were completely or partially soaked as follows: For complete soaked sponges: 2 ml thrombin solution (1000 IU/ml) was added to 20 ml L9 buffer to obtain 90 IU/ml solution. The sponges were wetted, kneaded and soaked in this solution for about 1 min. The sponges absorbed approximately 2.5 ml which correspond to 35 IU/cm$^2$ (225 IU/inch$^2$). The partial soaked sponges were immersed in a 3×3×0.2 cm plastic tray containing 400 μl thrombin solution (1600 IU/ml) for about three min. The solution was absorbed by capillary action. In this way the sponge absorbs an average 140 mg liquid which corresponds to 225 IU/inch$^2$. Afterwards, the completely soaked sponges were dried in lyophilization and the partially soaked sponges were dried in a vacuum oven (both drying procedures were carried out as specified above in the method section).

Thrombin release from the sponges was tested by measuring thrombin clotting activity at various time points as specified in the method section.

The findings suggest that sponges prepared by complete soaking followed by lyophilization drying procedure release thrombin faster than sponges prepared by partial soaking and dried in a vacuum oven wherein the thrombin was gradually released.

Figure 11:
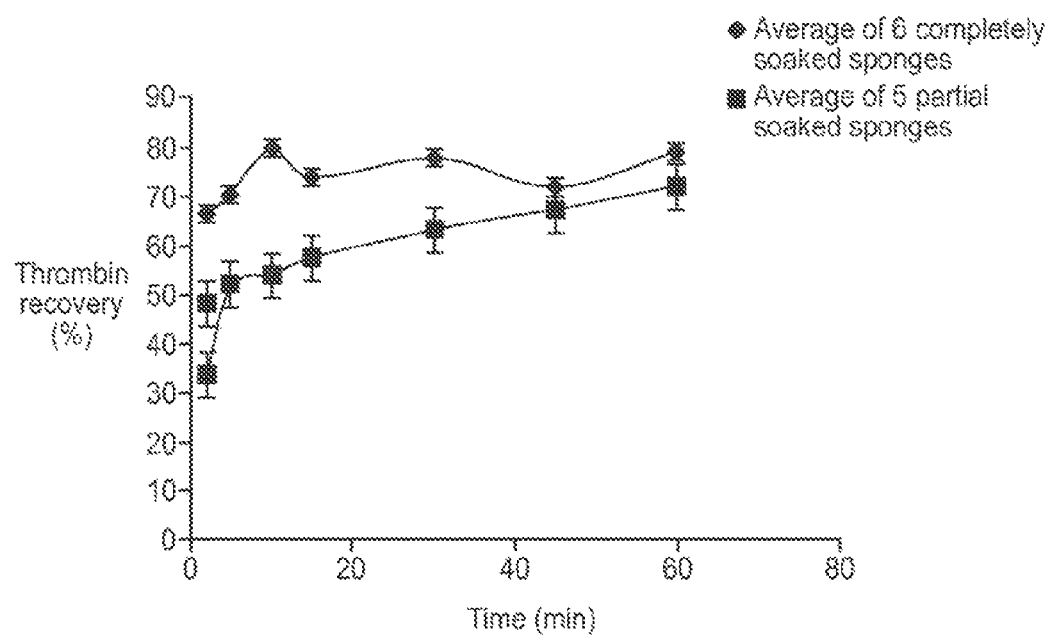
FIG. 11: shows the release of the active ingredient from complete soaked SPONGOSTAN® sponges dried by lyophilization compared to partially soaked sponges dried in a vacuum oven.

Furthermore, the results show that at the end of the testing both sponges had similar recovered activity indicating that sponges prepared by partial soaking followed by vacuum oven drying procedure preserve the thrombin activity (FIG. 11).

An in vivo evaluation of the haemostatic characteristics of these two gelatin sponges [complete soaking followed by lyophilization drying procedure (A) and partial soaking dried in a vacuum oven (B)] was done by measuring the blood loss in a Rat Kidney Hemorrhage Model as described above. The results are presented in Table 5.

TABLE 5

Blood Loss in Rat Kidney Model Using Different Gelatin Sponges.

| Sponge type | Blood Loss (g) | Average Blood Loss (g) |
| --- | --- | --- |
| Complete soaking + lyophilization (A) | 1.39, 4.08, 6.54, 0, 4.44, 1.7 | 3.02 ± 2.9 |
| Partial soaking + vacuum drying (B) | 0, 0.23, 2.82, 0.11, 5.45, 0.97 | 1.59 ± 2.16 |

*No statistical difference was found between the two groups at a significance level of 0.05 using t-TEST analysis.
*All experiments were preformed with SPONGOSTAN ® gelatin sponges consisting of 35 IU/cm$^2$ thrombin.

The trend shows that partially-soaked sponges are more efficient in preventing blood loss than completely-soaked sponges. In addition, the partially soaked sponges were also more malleable as compared to the completely soaked sponges following the drying step.

Example 9

Haemostatic Efficacy Achieved by a Gelatin Sponge Prepared by Partial Soaking and Vacuum Drying This example evaluates the haemostatic characteristics of a ready-to-use gelatin sponge prepared by partial soaking and vacuum drying using the Rat Kidney Hemorrhage Model described above.

The gelatin sponges were prepared as described in Example 8 (partial-soaked sponges). The total amount of thrombin applied to the wound-contacting surface of the sponge was 35 IU/cm$^2$. Table 6 summarizes the blood loss using the ready-to-use gelatin sponge.

TABLE 6

Blood Loss in Rat Kidney Model Using Different Gelatin Sponge Compositions.

| Sponge composition | Blood Loss (g) | Average Blood Loss (g) |
| --- | --- | --- |
| CONTROL SPONGE (A) | 2.84, 6.19, 6.2, 5.15 | 5.1 ± 1.58 |
| SPONGE + Thrombin (B) | No bleeding, 0.23, 2.82, 0.11, 5.45, 0.97 | 1.6 ± 2.16 |

*Group A vs. group B p = 0.0091 using t-TEST analysis.
*All experiments were preformed with SPONGOSTAN ® gelatin sponge consisting of 35 IU/cm$^2$ thrombin. SPONGOSTAN ® sponges without thrombin were used as the control group.

The above data demonstrates that gelatin sponge with thrombin (composition B) is more effective in preventing blood loss than control gelatin sponge (composition A) i.e., blood loss was significantly reduced using a gelatin sponge which comprises a thin layer of thrombin on one surface of the sponge.

Example 10

Roller Apparatus: Structure and Operation Technique

Structure: A roller apparatus was assembled using the following components:

Two rollers (60 mm length, Diameter 20 mm). One of the rollers was covered with a polypropylene net (see marking number 3 in FIG. 12; diagonal size: 1100 μm) and was used as the lower roller.

Bath [external dimenstions: 38×72×15 mm (W×L×H)]. The thickness of the wall is 3 mm. The bath can contain up to 9.5 ml liquid.

Tuning adjustment unit which enable to change the gap space between the upper and the lower roller. The unit is composed of two screws and two adjusting plate (one at each side).

Base-plate for supporting the whole structure.

Motor having a speed range of 5 to 200 RPM.

The two rollers were positioned one above the other (1 and 2—lower and upper rollers, respectively) on the base-plate (4) using two carry supports (5a-b) at each end of the rollers. 5a—holds the lower roller and 5b—holds the upper movable roller. Between components 5a and 5b there are springs (6; two at each side) to maintain the clearance between components 5a and 5b.

The carrying supports were fixed to the base-plate using screws (two at each end of the rollers; 7). The lower roller is stationary on y axis and the upper roller is capable of reciprocating on y axis above the lower roller. In the center of each carry support there is a tuning adjustment screw (8) capable of moving component 4b resulting in decrease or increase in the gap between the two rollers. An adjusting plate (9) supports the tuning adjustment screw. A shaft (10) is connected to the lower roller through component 5a. The shaft is rotated by a motor, the speed of which can be controlled. Actuation of the apparatus results in counter-rotation of the two rollers. The bath (11) is positioned under the lower roller. Under the base-plate, at each corner, there are screws (not shown) which are used to attain leveling of the apparatus.

This roller apparatus fits any substrate within the following ranges: width: up to 60 mm; length: not limited; thickness: sheet like up to 30 mm. The apparatus dimensions can be adjusted to any substrate of varied width and thickness.

Operation Technique. The gap between the bottom roller and the upper roller was adjusted, the apparatus was positioned on a hard level surface and the leveling was adjusted using a leveling tool. The solution (about 9.5 ml) was poured into the bath and the apparatus was operated for about five minutes to reach a liquid equilibrium uptake between the lower roller and the bath. Then, the sponge was passed between the two rollers (see marking number 12 in FIG. 12) and the solution was passively deposited onto the bottom side of the sponge by capillary force. During the wetting step the upper roller applies pressure onto the sponge thereby enabling the sponge to be ejected from the apparatus and controlling the liquid uptake capability of the sponge. The sponge was weighed before and after the wetting process and the liquid uptake was calculated by subtracting the weight of the sponge following the wetting step from its weight prior to wetting. Prior to an additional feeding, solution was added to the bath to maintain the reservoir and the rollers were operated to reach a liquid equilibrium uptake between the lower roller and the bath.

Figure 12:
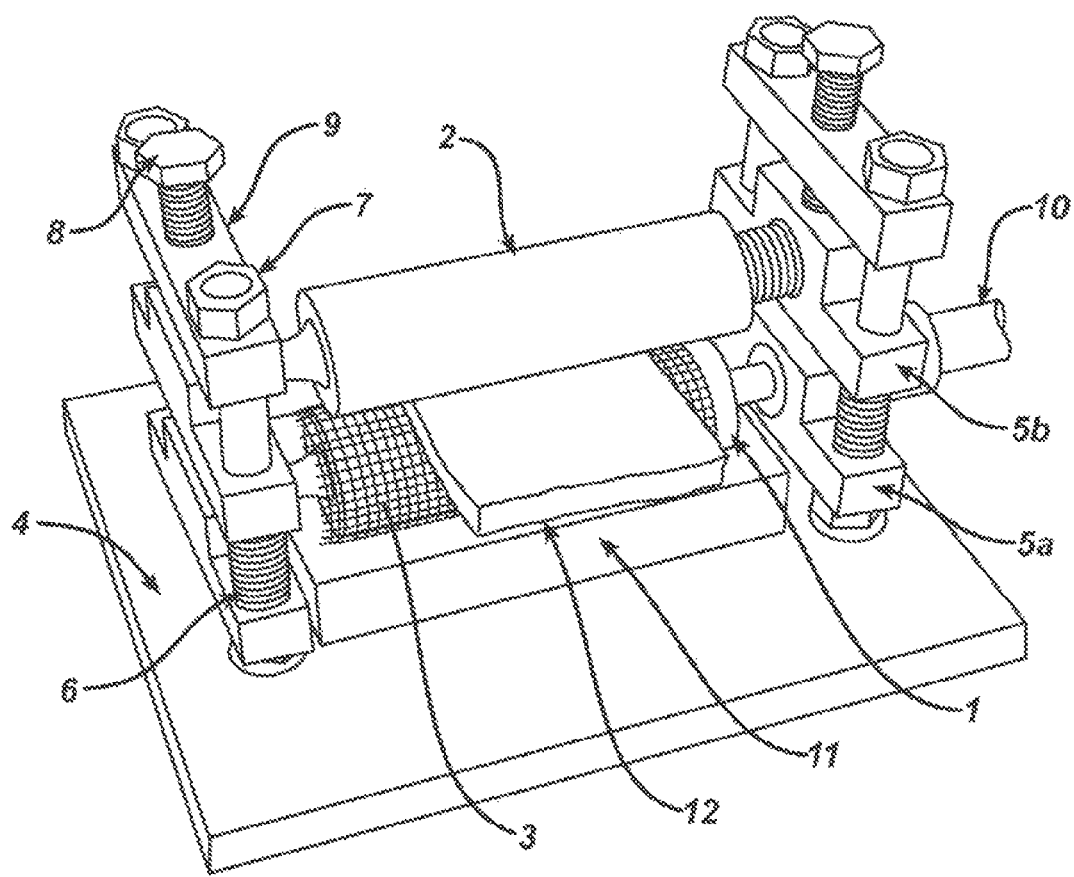
FIG. 12: shows the assembled apparatus used in these experiments. 1—lower roller; 2—upper roller; 3—polypropylene net; 4—base-plate; 5—carry supports (5a—holds the lower roller and 5b—holds the upper movable roller); 6—springs; 7—screws; 8—adjustment screw; 9—adjusting plate; 10—shaft; 11—bath; 12—sponge.

FIG. 12 shows the assembled apparatus used in these experiments. 1—lower roller; 2—upper roller; 3—polypropylene net; 4—base-plate; 5—carry supports (5a—holds the lower roller and 5b—holds the upper movable roller); 6—springs; 7—screws; 8—adjustment screw; 9—adjusting plate; 10—shaft; 11—bath; 12—sponge.

Example 11

Thickness Measurements of Commercial Sponges

The Gap Between the Upper and the Lower Roller Needs to be Adjusted Before Feeding the sponge into the roller apparatus. Since there may be variations in the thickness of the sponge, the thickness was measured in 21 sponges (SPONGOSTAN®; 5×7×1 cm) using a digital caliper. The measurement was carried out at the center of the sponge. The results are listed in Table 7.

TABLE 7

The Thickness of the Commercial Sponge.

| Thickness (mm) | Average Thickness (mm) |
|---|---|
| 8.7, 9.4, 9.6, 10.1, 10.2, 10.1, 10.1, 10.3, 10.3, 10.3, 10.3, 10.4, 10.7, 10.6, 9.7, 9.8, 10, 10.6, 10.3, 10.3, 10.3 | 10.1 ± 0.45 |

The results show that there is a variation in the thickness of the sponges; thus, it is advantages to monitor the thickness of the sponge before passing it through the apparatus. Since the average thickness was 10.1±0.45, henceforth the gap between the rollers was adjusted to 10 mm.

Example 12

Applying a Thrombin Coating Using the Roller Apparatus

The present example illustrates that the liquid uptake volume into the sponge during the wetting process can be controlled by using a roller apparatus.

The texture profile of the sponges were observed to vary between different areas of the sponge: the upper region of the sponge had a low density having large pores (referred to herein as "open side") while the bottom side was denser having smaller pores (referred to herein as "closed side").

The apparatus was operated as specified above (Example 10). The sponges (SPONGOSTAN®; 5×7×1 cm) were inserted through the apparatus with the open side facing down. Concentrated thrombin solution (8000 IU/ml) was used as the coating solution.

The rollers speed was set to 20 RPM. Table 8 shows the thrombin solution uptake in two sets of experiments.

TABLE 8

Thrombin Uptake into the Open Side of the Sponge.

| Thrombin uptake (mg) | Average Uptake (mg) |
|---|---|
| Experiment No. 1: | |
| 142.5, 150.5, 142.9, 142.5 | 144.6 ± 3.4 |
| Experiment No. 2: | |
| 152.3, 136.7, 153.4, 156.9, 148.1, 133.6, 150.1, 133.8, 141.7 | 145.2 ± 8.9 |

The results show that the thrombin uptake was substantially the same in all the tested sponges. These results were verified using thrombin solution in a concentration of 4000 IU/ml. In this study the liquid applying step was as follow: the sponge (SPONGOSTAN®; 5×7×1 cm) was fed into the apparatus with the open side facing down, dried in a vacuum-oven at about 0.4 mbar for 3 hours and passed again with the close side facing down. The rollers speed was set to 20 RPM. Each sponge was weighed before and after each feeding and the net weight was calculated. The results are demonstrated in Table 9 below.

TABLE 9

Thrombin Uptake into the Open and Closed Side of the Sponge.

| Sponge No. | Thrombin Solution Uptake (mg) | | |
|---|---|---|---|
| | Open Side | Close Side | Total |
| 1 | 146.1 | 189.1 | 335.2 |
| 2 | 131.8 | 164.5 | 296.3 |
| 3 | 138.9 | 142.2 | 281.1 |
| 4 | 149.8 | 181.2 | 331 |
| 5 | 130 | 167.4 | 297.4 |
| 6 | 128.7 | 149 | 277.7 |
| 7 | 144.6 | 147.1 | 291.7 |
| 8 | 147 | 152.3 | 299.3 |
| 9 | 126.1 | 162.1 | 288.2 |
| 10 | 134.4 | 182.6 | 317 |
| Average | 137.74 ± 6.3 | 163.75 ± 10.0 | 301.5 ± 6.6 |

The results of this study are in line with the previous result showing that the roller apparatus is an efficient method to apply liquid onto the surface of the sponge.

Example 13

The Effect of the Roller Speed During the Liquid Applying Step on the Liquid Uptake of the Sponge The purpose of the study was to determine the effect of roller speed on the liquid uptake of the sponge. The assessment was carried out using increasing roll speeds of 20 to 100 RPM. During the experiment, the sponges (SPONGOSTAN®; 5×7×1 cm) were inserted into the apparatus with the open or closed side facing down. The apparatus was operated as described in Example 10. The bath was filled with ultra filtrated L9 buffer solution.

Figure 13A:
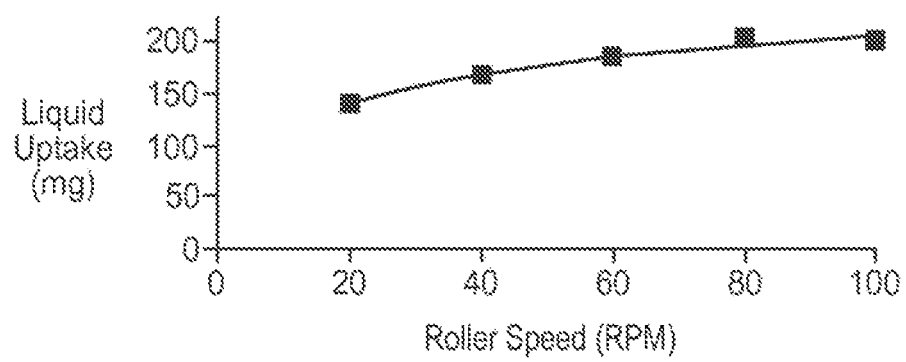
FIGS. 13A and B: show the liquid uptake of SPONGOSTAN® sponges in the various operating speeds (20-100 RPM) when fed into the apparatus either on its open (A) or closed side (B).
Figure 13B:
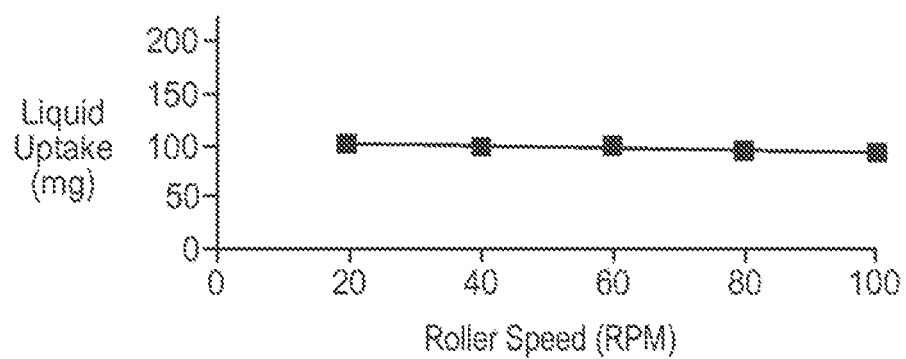

FIG. 13 shows the liquid uptake of the sponge in the various operating speeds when fed into the apparatus either on its open (A) or closed side (B).

It is apparent that an increase in the roller speed had a substantial effect on the liquid uptake when the sponge was inserted into the apparatus with the open side facing down. The liquid uptake by the sponge was shown to be directly proportional to the speed. In comparison, no significant difference was observed in the liquid uptake when the sponge was inserted with the closed side facing down.

Moreover, as was shown in this example, the closed side of the sponge exhibited a low liquid uptake in all tested speeds as compared to the open side. These finding indicate that the density of the sponge affects its liquid uptake capability; low density sponge often have more air holes as compared to dense sponges, thus are capable to absorb more liquid.

Note that in Example 12 the close side exhibited a slightly higher liquid absorption as compared to the open side (163.75±10.0 and 137.74±6.3, respectively). In this experiment the sponge was initially inserted into the apparatus on its open side and subjected to drying prior to be fed into the apparatus on its close side. These prior steps appear to change the liquid uptake capability of the sponge.

The example shows that the level of liquid applied to the sponge can be adjusted by changing the velocity of the roller.

Example 14

The Effect of the Characteristics of the Sponge and the Solution on the Liquid Uptake Capability of the Sponge The previous example shows that the density of the sponge affects its liquid absorption capability. The following example was carried out to verify these results and to further evaluate the effect of the solution characteristic (e.g. viscosity) on the liquid uptake. The apparatus was operated as described above. The bath was filled either with L9 buffer solution or with thrombin solution (4000 IU/ml) prepared as described above. The wetting step was as follow: the sponge (SPONGOSTAN®; 5×7×1 cm) was passed through the apparatus with the closed side facing down ($1^{st}$ pass), vacuum-dried as specified in the method section and passed again ($2^{nd}$ pass) with the open side facing down. The second feeding was carried out using the same solution as the first feeding. Each sponge was weighed before and after each feeding and the net weight was calculated. The procedure was carried out in different roller speed (40 to 140 RPM).

Figure 14:
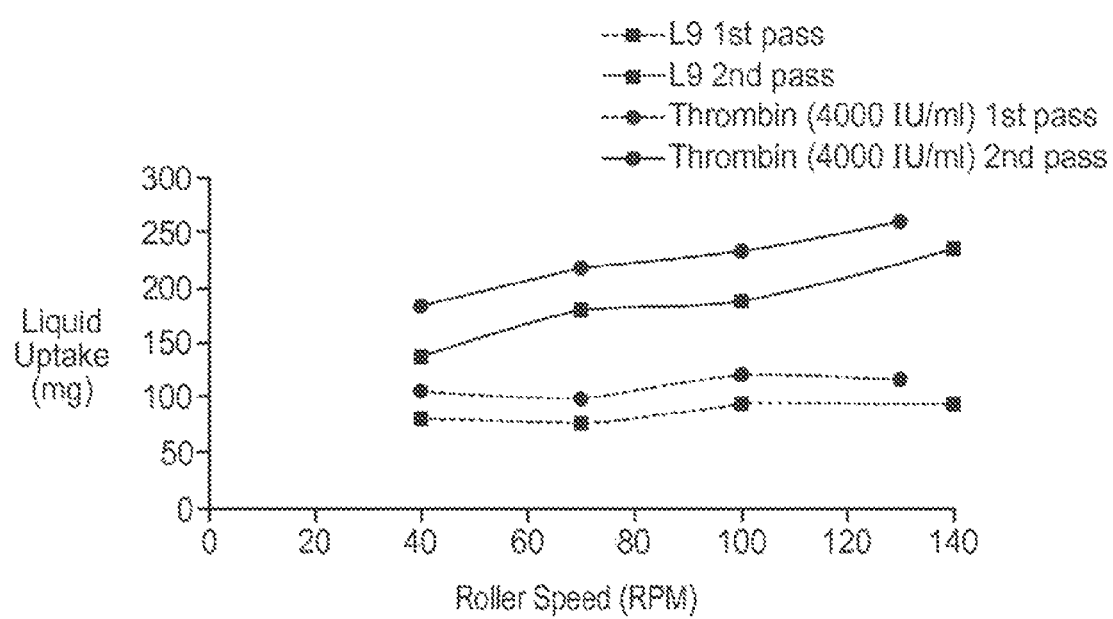
FIG. 14: shows the liquid uptake of the sponge vs. the roller speed using L9 buffer solution or thrombin solution (4000 IU/ml). The sponge were passed through the apparatus with the closed side facing down ($1^{st}$ pass), vacuum-dried and passed again with the open side facing down ($2^{nd}$ pass).

FIG. 14 shows the liquid uptake of the sponge vs. the roller speed using L9 buffer solution or thrombin solution (4000 IU/ml).

The results corroborate the previous results and show that the closed side of the sponge (the denser side) absorbs less liquid as compared to the open side. In addition, it is also apparent, as proved above, that unlike the open side the closed side exhibits similar liquid uptake in the different roller speeds.

Also, a higher liquid uptake was observed in both sides of the sponge when using the thrombin solution as the wetting solution. This may be as a result of the difference in the viscosity of the solutions (0.95 and 1.31 cPs for the L9 and thrombin solution, respectively). The viscosity was measured at 25° C. using a glass capillary viscometer according to the manufacturer's instructions). The results obtained indicate that in highly viscous solutions the liquid uptake is greater than in solutions with lower viscosity.

Example 15

Applying a Thrombin Coating Using the PipeJet™-Technology

The following example demonstrates application of thrombin solution onto a gelatin sponge using the PipeJet™-technology. This technology is a valve free method for non-contact dispensing of liquids in the range of a few nanoliters up to several microliters. The dispenser, which is connected to the reservoir, comprises a piston ("Piezo Stack Actuator") and a flexible polymer tube (the "pipe"). The piston is pressed against the tube and the liquid is expelled from the nozzle. When applying the solution, the substrate is moved and the liquid is distributed over the surface of the sponge (the dispenser is stationary). At first the platform carrying the sponge was moved on y axis followed by a one step movement on x axis (the distance between the dropping points are indicated below). These two steps were repeated until the sponge was fully covered. At each stopping point a drop was released. The volume dispensed by the PipeJet™ method is controlled by the amplitude of the actuator. Two sets of experiments were carried out both using 7×5×1 cm SPONGOSTAN® sponges weighing between 430 to 448 mg. In the first set of experiments the dispenser tube used had an internal diameter of 200 μm and the jet was programmed to the following parameters: dosage frequency: 37 Hz; drop volume: 7 nl; distance between the drops on x axis: 0.4 mm; distance between the drops on y axis: 0.4 mm. The group contained four different sponges; two were covered on their open side and two on their close side. In the second set of experiments the dispenser tube used had an internal diameter of 500 μm and the jet was programmed to the following parameters: dosage frequency: 90 Hz; drop volume: 44 nl. The group contained four different sponges of which in three of the sponges (one coated on its open side and two on their close side) the distance was set as follows: x axis—1 mm; y axis—1 mm. An additional sponge (sample 8) was covered on its open side wherein the distance on the x axis was set to 1 mm and the distance on y axis was set to 0.4 or 1 mm (in the first row a distance of 0.4 mm was used and in the secand row a distance of 1 mm was used and so on).

In both experiments the coating material used was 8000 IU/ml thrombin solution containing 0.01% indigo carmine (Amresco code cat No 9827-25g), the process speed was set to 1500 steps/sec, the total volume dispensed was ~150 μl and the Pipejet™ P9 Module was used. Following the liquid application step the sponges were vacuum-dried as described above.

A visual inspection of the dried sponge revealed that in each sponge the thrombin layer was relatively uniformly distributed throughout the surface of the sponge. In order to quantify the uniformity of the layer two samples (1.5×1.5 mm) were cut from the corner and the middle of the dried sponge (two sponges from each experiment were evaluated) and thrombin activity was determined as specified in the method section. The percentage of the expected thrombin activity of the sample area (100%) was calculated for each sample. The delta between the measured activity of the corner and center sample is listed in Table 10 below.

TABLE 10

The Uniform Distribution of Thrombin throughout the Surface of the Sponge.

| Sponge Description | Δ Thrombin Activity Between the Corner and Center Sample (%) |
| --- | --- |
| Experiment No. 1; open side | 2 |
| Experiment No. 1; close side | 1 |
| Experiment No. 2; close side | 3 |
| Experiment No. 2; open side; (sample 8) | 3 |

The results show that thrombin activity was substantially the same in the corner and center samples (a Δ of less than 3 was observed in all tested sponges) of each sponge indicating that the active ingredient is evenly distributed on the surface of the sponge. These results demonstrate that the PipeJet™-technology is an efficient and an accurate method which enables control of the dispensed volume, consequently resulting in a homogenous distribution of the liquid comprising the active ingredient on the surface of the sponge.

Example 16

The Stability of the Protein Layer on the Surface of the Sponge

This example examines the stability of the thrombin layer on the surface of the ready-to-use gelatin sponge. For this purpose, 150 μl thrombin solution (8000 IU/ml prepared as described above) was applied to the open side of SPONGOSTAN® sponges (7×5×1 cm) using the roller apparatus as described above. Following the wetting step, the sponges were vacuum-dried as specified in the method section. Stability test was carried out as specified in the method section. The measurements were carried out on two different sponges prepared as described above. 3 to 4 different samples were taken from each sponge individually. The results are presented in Table 11 below.

TABLE 11

The Stability of the Protein Layer.

| | Pre-drop weight (mg) | Post-drop weight (mg) | Powder loss (mg) | Weight reduction (%) |
|---|---|---|---|---|
| Sponge No. I | | | | |
| Sample 1 | 33.9 | 33.8 | 0.1 | 0.29 |
| Sample 2 | 34.4 | 33.6 | 0.8 | 2.33 |
| Sample 3 | 29.2 | 28.9 | 0.3 | 1.03 |
| Sample 4 | 32.9 | 32.6 | 0.3 | 0.91 |
| Average | | | | 1.14 |
| Sponge No. II | | | | |
| Sample 1 | 18.4 | 17.7 | 0.7 | 3.80 |
| Sample 2 | 26.4 | 26 | 0.4 | 1.52 |
| Sample 3 | 26.4 | 26.3 | 0.1 | 0.38 |
| Average | | | | 1.90 |

The results show that the weight reduction of the sponges was 1.14 and 1.90% for sponge I and II, respectively.

These results indicate that the protein layer is stable and the protein does not undergo flaking, the protein layer is continuous, does not break and/or crumble into individual pieces.

Example 17

The Effect of the Liquid Volume Uptake into the Sponge on its Mechanical Properties The following example evaluates the effect of the liquid volume uptake into the sponge on the original characteristics of the sponge e.g. flexibility.

For this purpose, SPONGOSTAN® sponges were cut to a size of 5.5×2×1 cm and partially soaked in a tray [3×3×0.2 (depth) cm] containing L9 buffer solution until an uptake of 74, 111 and 176 was obtained. No liquid was applied to the control SPONGOSTAN® sponges. The weight of the sponges was measured before and after the wetting step. Then, the sponges were vacuum-dried, their height was measured and the three point bending flexural test was carried out (see methods section above). The liquid uptake during the wetting step, the sponge thickness following the drying step, and the modulus of elasticity of the ready-to-use sponges are listed in Table 12 below.

TABLE 12

The Modulus of Elasticity of the Ready-To-Use Sponges.

| Liquid uptake (μl) | Thickness (mm) | Modulus of elasticity (gf/mm) |
|---|---|---|
| 0 | 10 | 62.2 |
| 0 | 10 | 54.6 |
| 74 | 9 | 47.6 |
| 111 | 9 | 60.8 |
| 176 | 8 | 43.9 |

The results reveal that all tested samples have approximately the same flexural strength indicating that the flexibility of the ready-to-use sponges is substantially retained following the wetting and drying step.

The invention claimed is:

1. A method for promoting blood coagulation, comprising administering to a wound or a bleeding site a cross-linked gelatin sponge obtained by the steps of:
   a) providing a cross-linked gelatin sponge having at least one surface;
   b) homogenously applying an aqueous liquid comprising a protein or peptide active ingredient to said at least one surface of said sponge, wherein the volume of the liquid intake into said surface of said sponge is equal to or less than 5% of the volume of the sponge in a); and
   c) drying the sponge by a drying step selected from the group consisting of thermal drying, vacuum drying and freeze drying, wherein the obtained dry cross linked gelatin sponge comprises a stable layer of protein or peptide active ingredient on at least one surface of the sponge, the layer having an average thickness of not more than about 24% of the overall thickness of the sponge, wherein said layer is substantially homogenously distributed throughout said surface; and the thickness and the flexibility of the sponge are substantially similar to those found in the original counterpart non-layered gelatin sponge.

2. The method according to claim 1, wherein wetting agents are absent from said layer.

3. The method according to claim 1, wherein the active ingredient comprises thrombin.

4. The method according to claim 1, wherein the thrombin activity is in the range of from about 1 to about 300 IU/cm$^2$, in the range of from about 10 to about 40 IU/cm$^2$, or in the range of from about 20 to about 40 IU/cm$^2$.

* * * * *